United States Patent
Demarco et al.

(10) Patent No.: US 9,596,852 B2
(45) Date of Patent: *Mar. 21, 2017

(54) TEMPLATE-FIXED PEPTIDOMIMETICS WITH ANTIMICROBIAL ACTIVITY

(71) Applicants: POLYPHOR LTD., Allschwil (CH); UNIVERSITAET ZUERICH, Zurich (CH)

(72) Inventors: Steven J. Demarco, Dietgen (CH); Wim Vrijbloed, Moehlin (CH); Ricardo Dias, Binningen (CH); John Anthony Robinson, Wermatswil (CH); Nityakalyani Srinivas, Basel (CH); Frank Gombert, Huttingen (DE); Daniel Obrecht, Baettwil (CH)

(73) Assignees: POLYPHOR LTD., Allschwil (CH); UNIVERSITAET ZUERICH, Zurich (CH)

( * ) Notice: Subject to any disclaimer, the term of this patent is extended or adjusted under 35 U.S.C. 154(b) by 162 days.

This patent is subject to a terminal disclaimer.

(21) Appl. No.: 14/175,193

(22) Filed: Feb. 7, 2014

(65) Prior Publication Data

US 2014/0187472 A1 Jul. 3, 2014

Related U.S. Application Data

(62) Division of application No. 12/161,065, filed as application No. PCT/CH2007/000017 on Jan. 15, 2007, now Pat. No. 8,685,922.

(30) Foreign Application Priority Data

Jan. 16, 2006 (WO) .................. PCT/CH06/00036

(51) Int. Cl.
| | |
|---|---|
| *C07K 7/64* | (2006.01) |
| *A01N 43/36* | (2006.01) |
| *C07K 1/10* | (2006.01) |
| *C07K 7/06* | (2006.01) |
| *C07K 7/08* | (2006.01) |
| *C07K 14/00* | (2006.01) |

(52) U.S. Cl.
CPC ............ *A01N 43/36* (2013.01); *C07K 1/10* (2013.01); *C07K 7/06* (2013.01); *C07K 7/08* (2013.01); *C07K 7/64* (2013.01); *C07K 14/001* (2013.01)

(58) Field of Classification Search
CPC ... C07K 7/06; C07K 7/08; C07K 1/10; C07K 14/001; C07K 7/64; A01N 43/36
See application file for complete search history.

(56) References Cited

U.S. PATENT DOCUMENTS

| | | |
|---|---|---|
| 6,878,804 B1 | 4/2005 | Robinson et al. |
| 7,091,313 B2 | 8/2006 | Robinson et al. |
| 7,253,146 B2 | 8/2007 | Obrecht et al. |
| 7,417,024 B2 | 8/2008 | Obrecht et al. |
| 7,582,604 B2 | 9/2009 | Vrijbloed et al. |
| 7,786,078 B2 | 8/2010 | Zumbrunn et al. |
| 7,838,496 B2 | 11/2010 | Zumbrunn et al. |
| 7,855,179 B2 | 12/2010 | Vrijbloed et al. |
| 7,994,118 B2 | 8/2011 | Vrijbloed et al. |
| 8,399,611 B2 | 3/2013 | Obrecht et al. |
| 8,629,112 B2 | 1/2014 | Gombert et al. |
| 8,633,163 B2 | 1/2014 | Obrecht et al. |
| 8,642,560 B2 | 2/2014 | Vrijbloed et al. |
| 8,658,604 B2 | 2/2014 | Demarco et al. |
| 8,685,922 B2 | 4/2014 | Demarco et al. |
| 2010/0056432 A1 | 3/2010 | Vrijbloed et al. |
| 2011/0135576 A1 | 6/2011 | Demarco et al. |
| 2011/0230426 A1 | 9/2011 | Obrecht et al. |
| 2011/0245155 A1 | 10/2011 | Zumbrunn et al. |
| 2011/0312879 A1 | 12/2011 | Gombert et al. |
| 2011/0319291 A1 | 12/2011 | Vrijbloed et al. |
| 2012/0135942 A1 | 5/2012 | Obrecht et al. |
| 2012/0202821 A1 | 8/2012 | Obrecht et al. |
| 2012/0270881 A1 | 10/2012 | Obrecht et al. |
| 2012/0283168 A1 | 11/2012 | Jung et al. |
| 2012/0283196 A1 | 11/2012 | Barthélémy et al. |
| 2013/0150299 A1 | 6/2013 | Obrecht et al. |
| 2013/0189363 A1 | 7/2013 | Obrecht et al. |
| 2013/0225506 A1 | 8/2013 | Gombert et al. |
| 2014/0087994 A1 | 3/2014 | Demarco et al. |
| 2014/0107031 A1 | 4/2014 | Obrecht et al. |

OTHER PUBLICATIONS

U.S. Appl. No. 14/555,796, filed Nov. 28, 2014, Obrecht, et al.
U.S. Appl. No. 14/175,160, filed Feb. 7, 2014, Demarco, et al.
U.S. Appl. No. 14/100,878, filed Dec. 9, 2013, Demarco, et al.
U.S. Appl. No. 14/124,508, filed Mar. 18, 2014, Obrecht, et al.

*Primary Examiner* — Suzanne Ziska
*Assistant Examiner* — Thurman Wheeler
(74) *Attorney, Agent, or Firm* — Oblon, McClelland, Maier & Neustadt, L.L.P.

(57) ABSTRACT

Template-fixed β-hairpin peptidomimetics of the general formula

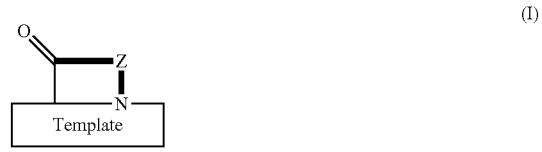

(I)

wherein Z is a template-fixed chain of 12 α-amino acid residues which, depending on their positions in the chain (counted starting from the N-terminal amino acid) are Gly, or Pro, or of certain types which, as the remaining symbols in the above formula, are defined in the description and the claims, and salts thereof, have the property to selectively inhibit the growth of or to kill microorganisms such as *Pseudomonas aeruginosa*. They can be used as disinfectants for foodstuffs, cosmetics, medicaments or other nutrient-containing materials, or as medicaments to treat or prevent infections.

These β-hairpin peptidomimetics can be manufactured by processes which are based on a mixed solid- and solution phase synthetic strategy.

10 Claims, No Drawings

TEMPLATE-FIXED PEPTIDOMIMETICS WITH ANTIMICROBIAL ACTIVITY

CONTINUING APPLICATION INFORMATION

The present application is a divisional of U.S. application Ser. No. 12/161,065, filed on May 17, 2010, which is a national stage of international application No. PCT/CH07/00017, filed on Jan. 15, 2007, which claims benefit to international application No. PCT/CH06/0036, filed on Jan. 16, 2006.

The present invention provides template-fixed β-hairpin peptidomimetics incorporating a template-fixed chain of 12 α-amino acid residues which, depending on their positions in the chain, are Gly or Pro, or of certain types, as defined herein below. These template-fixed β-hairpin mimetics have a selective antimicrobial activity. In addition, the present invention provides efficient synthetic processes by which these compounds can, if desired, be made in parallel library-format. These β-hairpin peptidomimetics show improved efficacy, bioavailability, half-life and most importantly a significantly enhanced ratio between antibacterial activity on the one hand, and hemolysis of red blood cells on the other.

The growing problem of microbial resistance to established antibiotics has stimulated intense interest in developing novel antimicrobial agents with new modes of action (H. Breithaupt, *Nat. Biotechnol.* 1999, 17, 1165-1169). One emerging class of antibiotics is based on naturally occurring cationic peptides (T. Ganz, R. I. Lehrer, *Mol. Medicine. Today* 1999, 5, 292-297; R. M. Epand, H. J. Vogel, *Biochim. Biophys. Acta* 1999, 1462, 11-28). These include disulfide-bridged β-hairpin and β-sheet peptides (such as the protegrins [V. N. M.; O. V. Shamova, H. A. Korneva, R. I. Lehrer, *FEBS Lett.* 1993, 327, 231-236], tachyplesins [T. Nakamura, H. Furunaka, T. Miyata, F. Tokunaga, T. Muta, S. Iwanaga, M. Niwa, T. Takao, Y. Shimonishi, Y. *J. Biol. Chem.* 1988, 263, 16709-16713], and the defensins [R. I. Lehrer, A. K. Lichtenstein, T. Ganz, *Annu. Rev. Immunol.* 1993, 11, 105-128], amphipathic α-helical peptides (e.g. cecropins, dermaseptins, magainins, and mellitins [A. Tossi, L. Sandri, A. Giangaspero, *Biopolymers* 2000, 55, 4-30]), as well as other linear and loop-structured peptides. Although the mechanisms of action of antimicrobial cationic peptides are not yet fully understood, their primary site of interaction is the microbial cell membrane (H. W. Huang, *Biochemistry* 2000, 39, 8347-8352). Upon exposure to these agents, the cell membrane undergoes permeabilization, which is followed by rapid cell death. However, more complex mechanisms of action, for example, involving receptor-mediated signaling, cannot presently be ruled out (M. Wu, E. Maier, R. Benz, R. E. Hancock, *Biochemistry* 1999, 38, 7235-7242).

The antimicrobial activities of many of these cationic peptides usually correlate with their preferred secondary structures, observed either in aqueous solution or in membrane-like environments (N. Sitaram, R. Nagaraj, *Biochim. Biophys. Acta* 1999, 1462, 29-54). Structural studies by nuclear magnetic resonance (NMR) spectroscopy have shown that cationic peptides such as protegrin 1 (A. Aumelas, M. Mangoni, C. Roumestand, L. Chiche, E. Despaux, G. Grassy, B. Calas, A. Chavanieu, A. *Eur. J. Biochem.* 1996, 237, 575-583; R. L. Fahrner, T. Dieckmann, S. S. L. Harwig, R. I. Lehrer, D. Eisenberg, J. Feigon, *J. Chem. Biol.* 1996, 3, 543-550) and tachyplesin I (K. Kawano, T. Yoneya, T. Miyata, K. Yoshikawa, F. Tokunaga, Y. Terada, S. J. Iwanaga, S. *J. Biol. Chem.* 1990, 265, 15365-15367) adopt well defined β-hairpin conformations, due to the constraining effect of two disulfide bridges. In protegrin analogues lacking one or both of these disulfide bonds, the stability of the β-hairpin conformation is diminished, and the antimicrobial activity is reduced (J. Chen, T. J. Falla, H. J. Liu, M. A. Hurst, C. A. Fujii, D. A. Mosca, J. R. Embree D. J. Loury, P. A. Radel, C. C. Chang, L. Gu, J. C. Fiddes, *Biopolymers* 2000, 55, 88-98; S. L. Harwig, A. Waring, H. J. Yang, Y. Cho, L. Tan, R. I. Lehrer, R. J. *Eur. J. Biochem.* 1996, 240, 352-357; M. E. Mangoni, A. Aumelas, P. Charnet, C. Roumestand, L. Chiche, E. Despaux, G. Grassy, B. Calas, A. Chavanieu, *FEBS Lett.* 1996, 383, 93-98; H. Tamamura, T. Murakami, S. Noriuchi, K. Sugihara, A. Otaka, W. Takada, T. Ibuka, M. Waki, N. Tamamoto, N. Fujii, *Chem. Pharm. Bull.* 1995, 43, 853-858). Similar observations have been made in analogues of tachyplesin I (H. Tamamura, R. Ikoma, M. Niwa, S. Funakoshi, T. Murakami, N. Fujii, *Chem. Pharm. Bull.* 1993, 41, 978-980) and in hairpin-loop mimetics of rabbit defensin NP-2 (S. Thennarasu, R. Nagaraj, *Biochem. Biophys. Res. Comm.* 1999, 254, 281-283). These results show that the β-hairpin structure plays an important role in the antimicrobial activity and stability of these protegrin-like peptides. In the case of the cationic peptides preferring α-helical structures, the amphililic structure of the helix appears to play a key role in determining antimicrobial activity (A. Tossi, L. Sandri, A. Giangaspero, A. *Biopolymers* 2000, 55, 4-30). Gramicidin S is a backbone-cyclic peptide with a well defined β-hairpin structure (S. E. Hull, R. Karlsson, P. Main, M. M. Woolfson, E. J. Dodson, *Nature* 1978, 275, 206-275) that displays potent antimicrobial activity against gram-positive and gram-negative bacteria (L. H. Kondejewski, S. W. Farmer, D. S. Wishart, R. E. Hancock, R. S. Hodges, *Int. J Peptide Prot. Res.* 1996, 47, 460-466). The high hemolytic activity of gramicidin S has, however, hindered its widespread use as an antibiotic. Recent structural studies by NMR have indicated that the high hemolytic activity apparently correlates with the highly amphipathic nature of this cyclic β-hairpin-like molecule, but that it is possible to dissociate antimicrobial and hemolytic activities by modulating the conformation and amphiphilicity (L. H. Kondejewski, M. Jelokhani-Niaraki, Niaraki, S. W. Farmer, B. Lix, M. Kay, B. D. Sykes, R. E. Hancock, R. S. Hodges, *J. Biol. Chem.* 1999, 274, 13181-13192; C. McInnes L. H. Kondejewski, R. S. Hodges, B. D. Sykes, *J. Biol. Chem.* 2000, 275, 14287-14294).

A new cyclic antimicrobial peptide RTD-1 was reported recently from primate leukocytes (Y.-Q. Tang, J. Yuan, G. Ösapay, K. Ösapay, D. Tran, C. J. Miller, A. J. Oellette, M. E. Selsted, *Science* 1999, 286, 498-502. This peptide contains three disulfide bridges, which act to constrain the cyclic peptide backbone into a hairpin geometry. Cleavage of the three disulfide bonds leads to a significant loss of antimicrobial activity. Analogues of protegrins (J. P. Tam, C. Wu, J.-L. Yang, *Eur. J. Biochem.* 2000, 267, 3289-3300) and tachyplesins (J.-P. Tam, Y.-A. Lu, J.-L. Yang, *Biochemistry* 2000, 39, 7159-7169; N. Sitaram, R. Nagaraij, *Biochem. Biophys. Res. Comm.* 2000, 267, 783-790) containing a cyclic peptide backbone, as well as multiple disulfide bridges to enforce a amphiphilic hairpin structure, have also been reported. In these cases, removal of all the cystine constraints does not always lead to a large loss of antimicrobial activity, but does modulate the membranolytic selectivity (J. P. Tam, C. Wu, J.-L. Yang, *Eur. J. Biochem.* 2000, 267, 3289-3300).

A key issue in the design of new selective cationic antimicrobial peptides are bioavailability, stability and reduced haemolytic activity. The naturally occurring protegrins and tachyplesins exert a significant hemolytic activity against human red blood cells. This is also the case for protegrin analogues such as IB367 (J. Chen, T. J. Falla, H. J. Liu, M. A. Hurst, C. A. Fujii, D. A. Mosca, J. R. Embree, D. J. Loury, P. A. Radel, C. C. Chang, L. Gu, J. C. Fiddes, *Biopolymers* 2000, 55, 88-98; C. Chang, L. Gu, J. Chen, U.S. Pat. No. 5,916,872, 1999). This high hemolytic activity essentially obviates its use in vivo, and represents a serious disadvantage in clinical applications. Also, the antibiotic activity of analogues often decreases significantly with increasing salt concentration, such that under in vivo conditions (ca. 100-150 mM NaCl) the antimicrobial activity may be severely reduced.

Protegrin 1 exhibits potent and similar activity against gram-positive and gram-negative bacteria as well as fungi in both low- and high-salt assays. This broad antimicrobial activity combined with a rapid mode of action, and their ability to kill bacteria resistant to other classes of antibiotics, make them attractive targets for development of clinically useful antibiotics. The activity against gram-positive bacteria is typically higher than against gram-negative bacteria. However, protegrin 1 also exhibits a high hemolytic activity against human red blood cells, and hence a low selectivity towards microbial cells. Oriented CD experiments (W. T. Heller, A. J. Waring, R. I. Lehrer, H. W. Huang, *Biochemistry* 1998, 37, 17331-17338) indicate that protegrin 1 may exist in two different states as it interacts with membranes, and these states are strongly influenced by lipid composition. Studies of cyclic protegrin analogues (J.-P. Tam, C. Wu, J.-L. Yang, *Eur. J. Biochem.* 2000, 267, 3289-3300) have revealed, that an increase in the conformational rigidity, resulting from backbone cyclization and multiple disulfide bridges, may confer membranolytic selectivity that dissociates antimicrobial activity from hemolytic activity, at least in the series of compounds studied.

Protegrin 1 is an 18 residues linear peptide, with an amidated carboxyl terminus and two disulfide bridges. Tachyplesin I contains 17 residues, also has an amidated carboxyl terminus and contains two disulfide bridges. Recently described backbone-cyclic protegrin and tachyplesin analogues typically contain 18 residues and up to three disulfide bridges (J. P. Tam, C. Wu, J.-L. Yang, *Eur. J. Biochem.* 2000, 267, 3289-3300; J. P. Tam, Y.-A. Lu, J.-L. Yang, *Biochemistry* 2000, 39, 7159-7169; N. Sitaram, R. Nagaraij, *Biochem. Biophys. Res. Comm.* 2000, 267, 783-790).

Cathelicidin, a 37-residue linear helical-type cationic peptide, and analogues are currently under investigation as inhaled therapeutic agents for cystic fibrosis (CF) lung disease (L. Saiman, S. Tabibi, T. D. Starner, P. San Gabriel, P. L. Winokur, H. P. Jia, P. B. McGray, Jr., B. F. Tack, *Antimicrob. Agents and Chemother.* 2001, 45, 2838-2844; R. E. W. Hancock, R. Lehrer, *Trends Biotechnol.* 1998, 16, 82-88). Over 80% of CF patients become chronically infected with *pseudomonas aeruginosa* (C. A. Demko, P. J. Biard, P. B. Davies, *J. Clin. Epidemiol.* 1995, 48, 1041-1049; E. M. Kerem, R. Gold, H. Levinson, *J. Pediatr.* 1990, 116, 714-719). Other antimicrobial peptides against Pseudomonads (Y. H. Yau, B. Ho, N. S. Tan, M. L. Ng, J. L. Ding, *Antimicrob. Agents and Chemother.* 2001, 45, 2820-2825 and herein cited references), like FALL-39, SMAP-29, and lepidopteran cecropin display a few of the desired attributes like potent antimicrobial activity over a wide range of pH, rapid killing rate, and low hemolytic activity.

In the compounds described below, a new strategy is introduced to stabilize β-hairpin conformations in backbone-cyclic cationic peptide mimetics exhibiting selective antimicrobial activity. This involves transplanting the cationic and hydrophobic hairpin sequence onto a template, whose function is to restrain the peptide loop backbone into a hairpin geometry.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). Antibacterial template—fixed peptidomimetics and methods for their synthesis have been described in International Patent applications WO02/070547 A1 and WO2004/018503 A1 but these molecules do not exhibit high plasma stability selectivity and particularly high potency.

The methods described herein allow the synthesis and screening of large hairpin mimetic libraries, which in turn considerably facilitates structure-activity studies, and hence the discovery of new molecules with potent selective antimicrobial and very low hemolytic activity to human red blood cells. The present strategy allows to synthesize β-hairpin peptidomimetics with novel selectivities towards various multi-drug resistant *pseudomonas*-strains.

The β-hairpin peptidomimetics of the present invention are compounds of the general formula

(I)

wherein

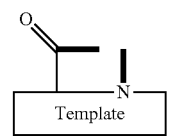

is a group of one of the formulae

(a1)

(a2)

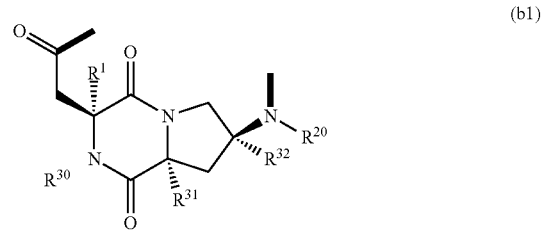

(b1)

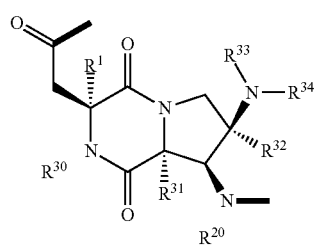
(b2)
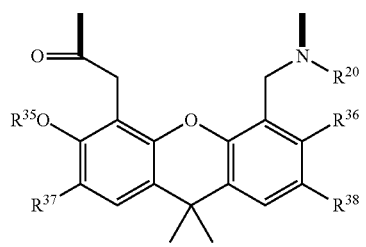
(c1)
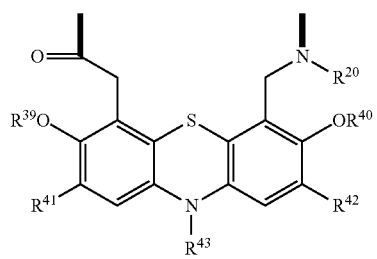
(c2)
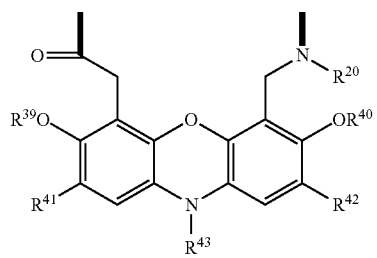
(c3)
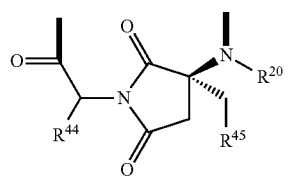
(d)
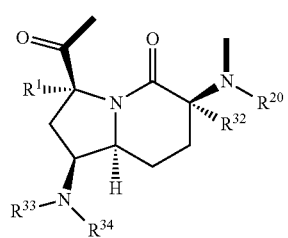
(e1)
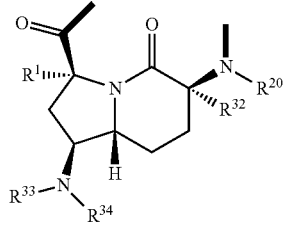
(e2)
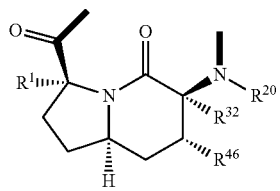
(e3)
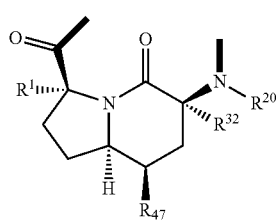
(e4)
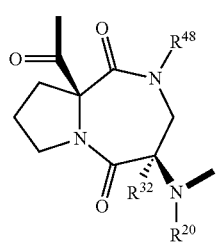
(f)
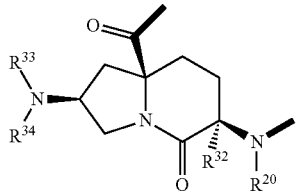
(g)
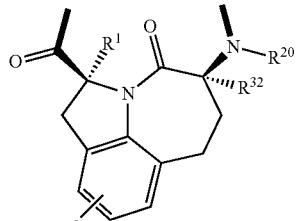
(h)
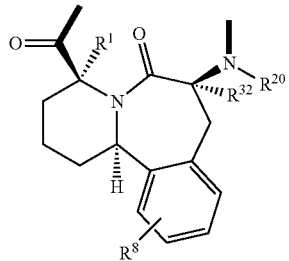
(i1)

-continued
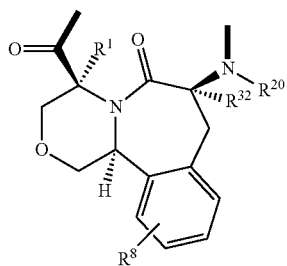
(i2)
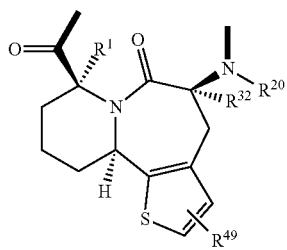
(i3)
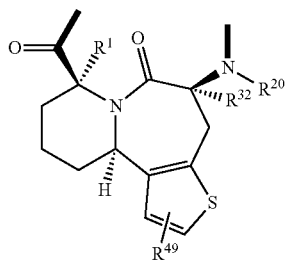
(i4)
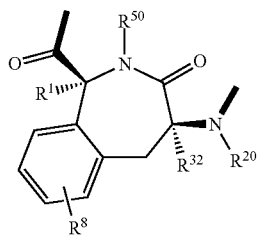
(j)
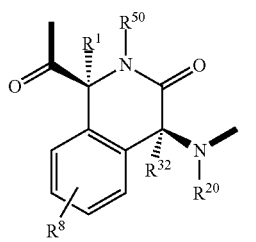
(k)
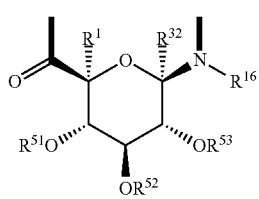
(l)
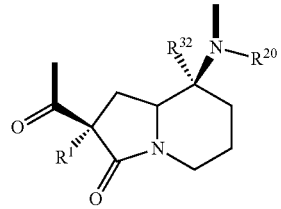
(m)
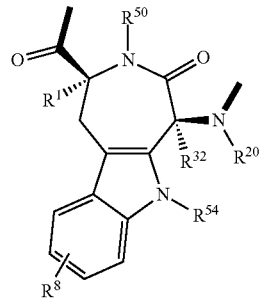
(n)
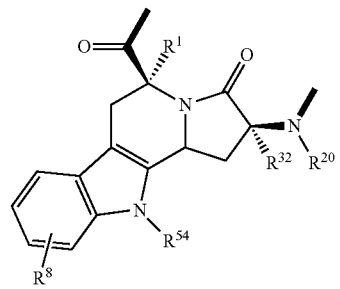
(o)
and
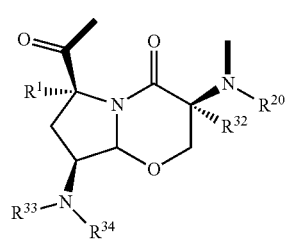
(p)
wherein
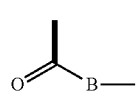
is the residue of an L-α-amino acid with B being a residue of formula —NR$^{20}$CH(R$^{71}$)— or the enantiomer of one of the groups A1 to A69 as defined hereinafter;
is a group of one of the formulae

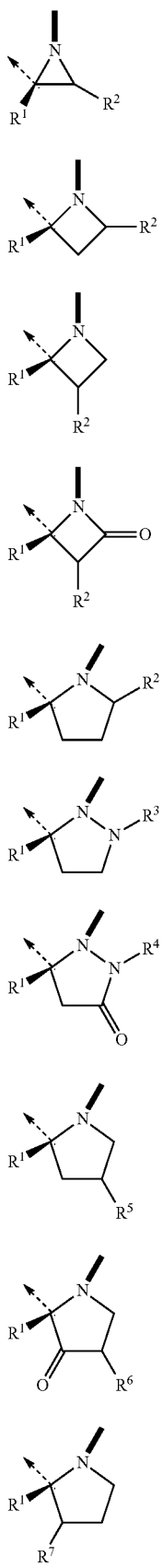
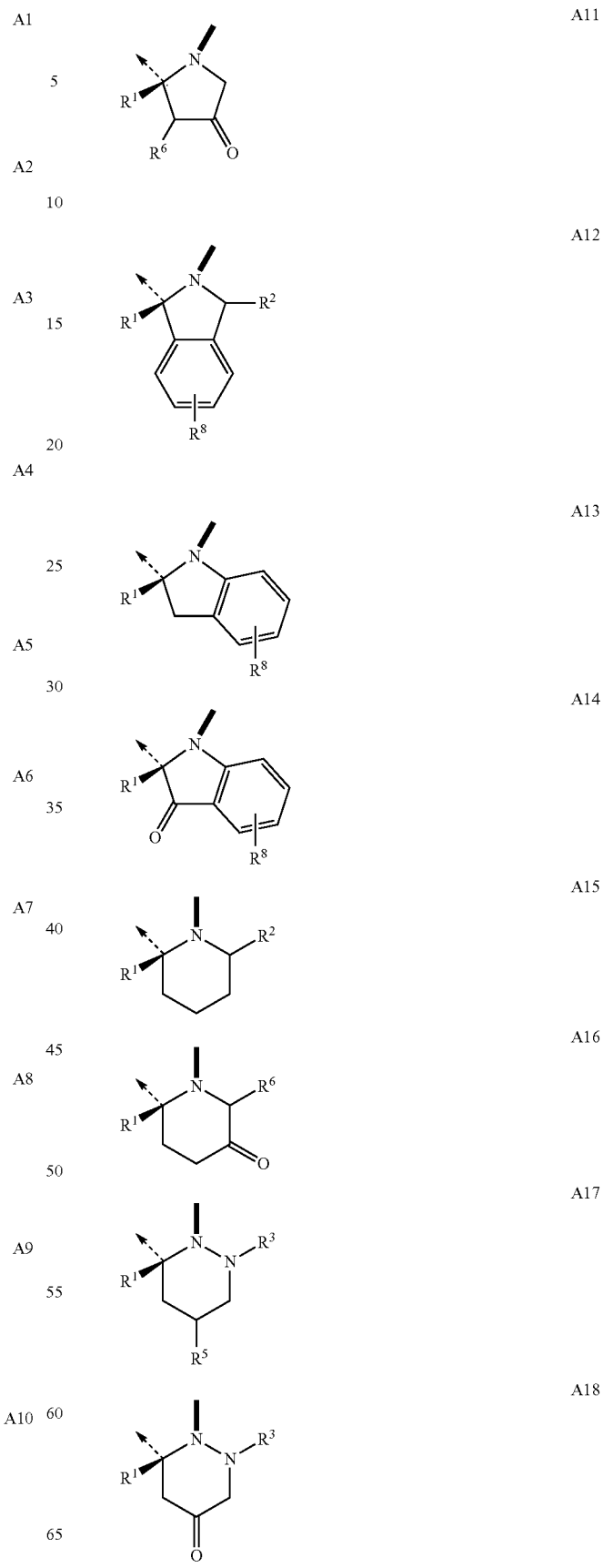

-continued
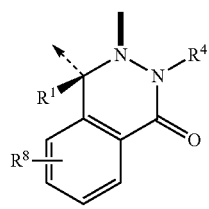
A19
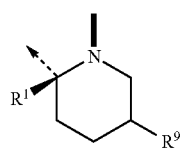
A20
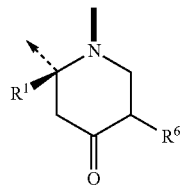
A21
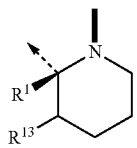
A27
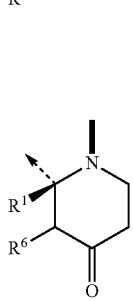
A28
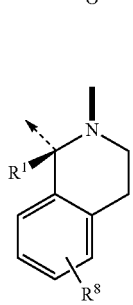
A29
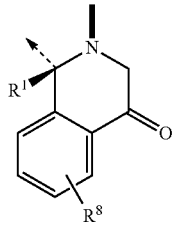
A30
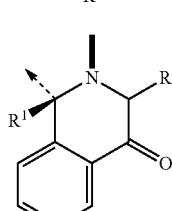
A31
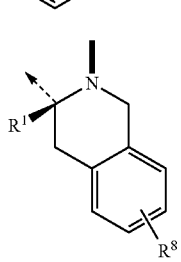
A32
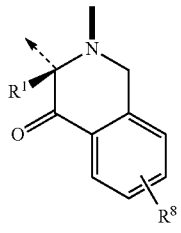
A33

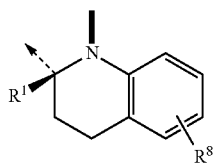 A34
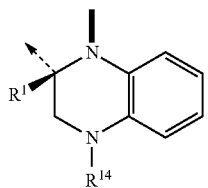 A35
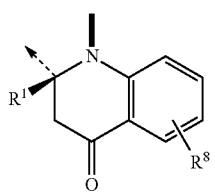 A36
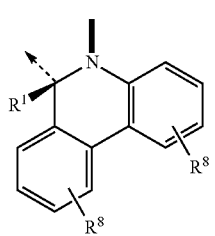 A37
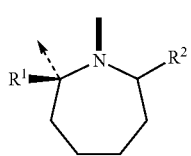 A38
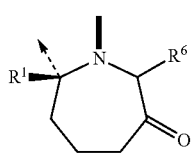 A39
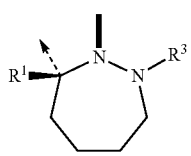 A40
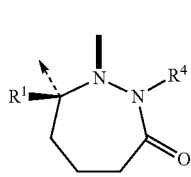 A41
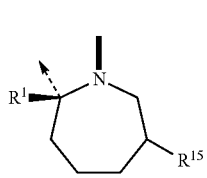 A42
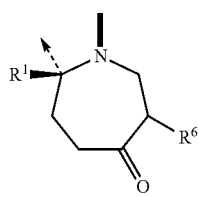 A43
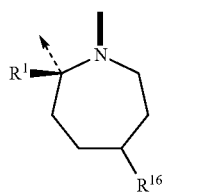 A44
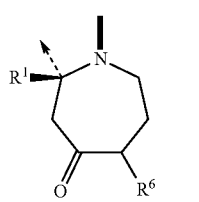 A45
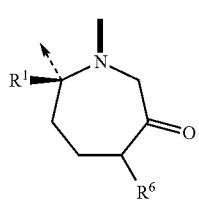 A46
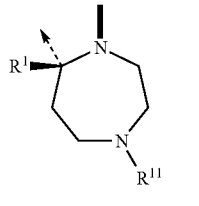 A47
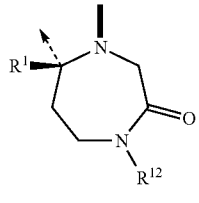 A48
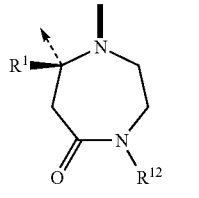 A49
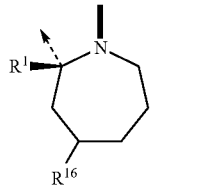 A50

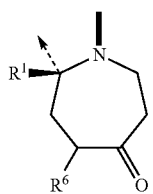 A51
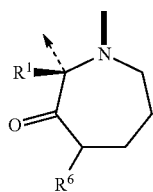 A52
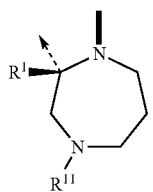 A53
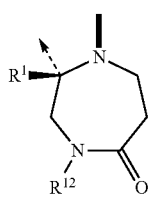 A54
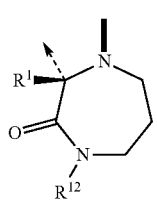 A55
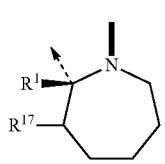 A56
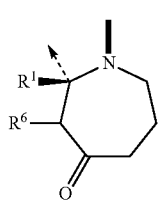 A57
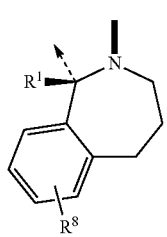 A58
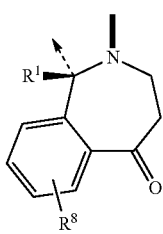 A59
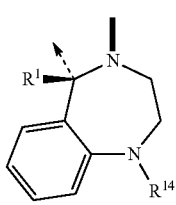 A60
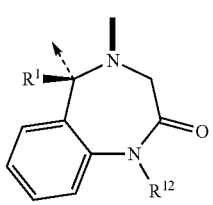 A61
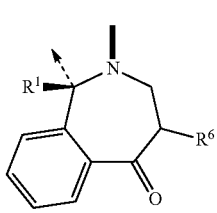 A62
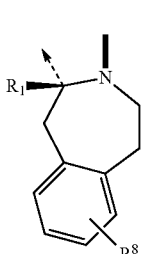 A63
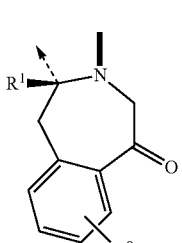 A64
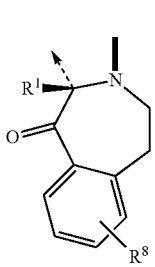 A65

-continued
A66 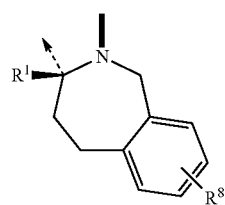
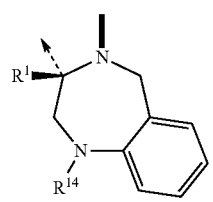
A67 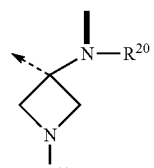
A68 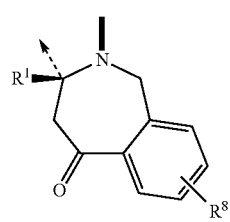
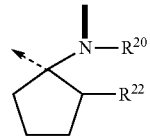
A69 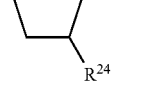
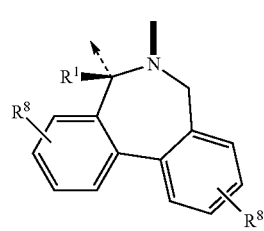
A70 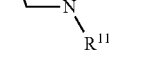
A71 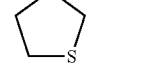
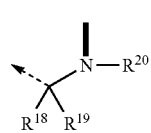
A72 
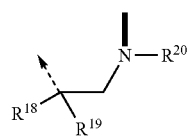
A73 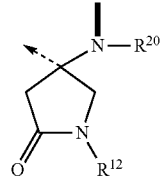
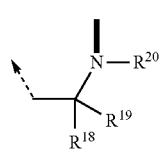
A74 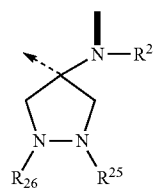
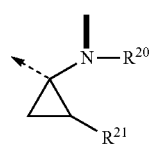
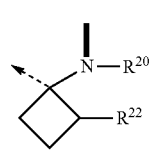
-continued
A75
A76
A77
A78
A79
A80
A81
A82
A83

A84 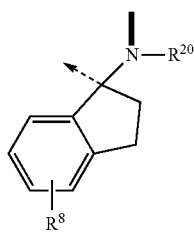
A85 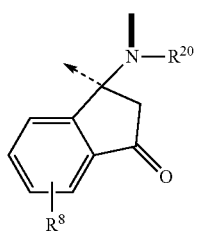
A86 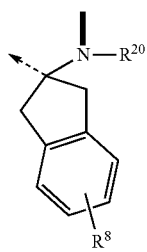
A87 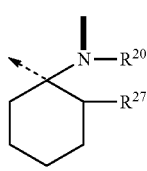
A88 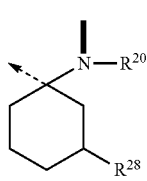
A89 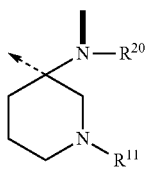
A90 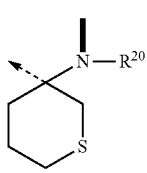
A91 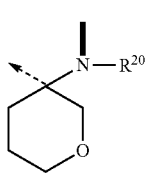
A92 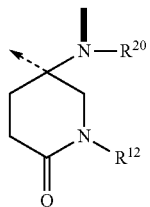
A93 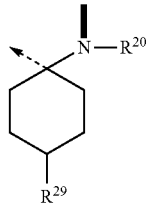
A94 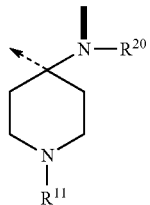
A95 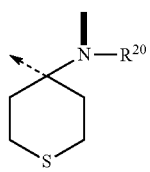
A96 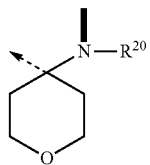
A97 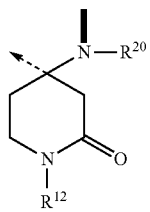
A98 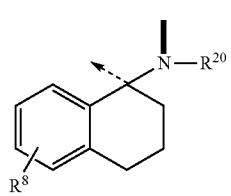
A99 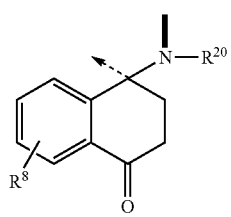

-continued

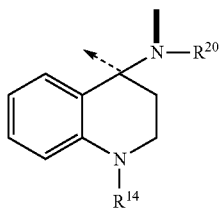

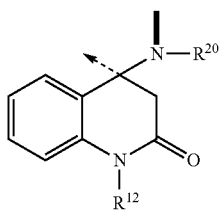

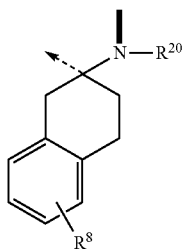

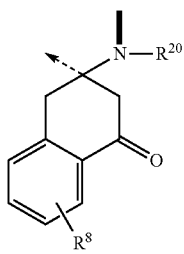

and

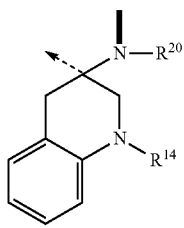

$R^1$ is H; lower alkyl; or aryl-lower alkyl;
$R^2$ is H; alkyl; alkenyl; —(CH$_2$)$_m$(CHR$^{61}$)$_s$OR$^{55}$; —(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; —(CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;
$R^3$ is H; alkyl; alkenyl; —(CH$_2$)$_m$(CHR$^{61}$)$_s$OR$^{55}$; —(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; (CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;
$R^4$ is H; alkyl; alkenyl; —(CH$_2$)$_m$(CHR$^{61}$)$_s$OR$^{55}$; —(CH$_2$)$_m$(CHR$^{61}$)$_s$SR$^{56}$;
—(CH$_2$)$_m$(CHR$^{61}$)$_s$NR$^{33}$R$^{34}$
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_p$(CHR$^{61}$)$_s$COOR$^{57}$; —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$ SO$_2$R$^{62}$; or —(CH$_2$)$_o$(CHR$^{61}$)$_s$C$_6$H$_{4l\ R}$$^8$;
$R^5$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;
$R^6$ is H; alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;
$R^7$ is alkyl; alkenyl; —(CH$_2$)$_q$(CHR$^{61}$)$_s$OR$^{55}$; —(CH$_2$)$_q$(CHR$^{61}$)$_s$NR$^{33}$R$^{34}$;
—(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$;
—(CH$_2$)$_r$(CHR$^{61}$)$_s$COOR$^{57}$; —(CH$_2$)$_r$(CHR$^{61}$)$_s$CONR$^{58}$R$^{59}$;
—(CH$_2$)$_r$(CHR$^{61}$)$_s$PO(OR$^{60}$)$_2$;
—(CH$_2$)$_r$(CHR$^{61}$)$_s$SO$_2$R$^{62}$; or —(CH$_2$)$_r$(CHR$^{61}$)$_s$C$_6$H$_4$R$^8$;
$R^8$ is H; Cl; F; CF$_3$; NO$_2$; lower alkyl; lower alkenyl; aryl; aryl-lower alkyl;
—(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)NR$^{33}$R$^{34}$
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)PO(OR$^{60}$)$_2$;
—(CH$_2$)$_o$(CHR$^{61}$)$_s$SO$_2$R$^{62}$; or —(CH$_2$)$_o$(CHR$^{61}$)$_s$COR$^{64}$;
$R^9$ is alkyl; alkenyl; —(CH$_2$)$_o$(CH—R$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;
$R^{10}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;

—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;

R$^{11}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$;
—(CH$_2$)$_m$(CHR$^{61}$)$_s$OCONR$^{33}$R$^{75}$;  —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(Cl$_2$)$_o$(CHR$^{61}$)$_s$C$_6$H$_4$R$^8$;

R$^{12}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$;
—(CH$_2$)$_m$(CHR$^{61}$)$_s$NR$^{33}$R$^{34}$;  —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_r$(CHR$^{61}$)$_s$COOR$^{57}$;
—(CH$_2$)$_r$(CHR$^{61}$)$_s$CONR$^{58}$R$^{59}$;  —(CH$_2$)$_r$(CHR$^{61}$)$_s$PO(OR$^{60}$)$_2$;  —(CH$_2$)$_r$(CHR$^{61}$)$_s$ SO$_2$R$^{62}$; or —(CH$_2$)$_r$(CHR$^{61}$)$_s$C$_6$H$_4$R$^8$;

R$^{13}$ is alkyl; alkenyl; —(CH$_2$)$_q$(CHR$^{61}$)$_s$ OR$^{55}$; —(CH$_2$)$_q$(CHR$^{61}$), SR$^{56}$
—(CH$_2$)$_q$(CHR$^{61}$)$_s$NR$^{33}$R$^{34}$
—(CH$_2$)$_q$(CHR$^{61}$)$_s$OCONR$^{33}$R$^{75}$;  —(CH$_2$)$_q$(CHR$^{61}$)$_s$NR$^{20}$CONR$^{33}$R$^{82}$;
—(CH$_2$)$_q$(CHR$^{61}$)$_s$COOR$^{51}$;  —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$ SO$_2$R$^{62}$; or —(CH$_2$)$_q$(CHR$^{61}$)$_s$C$_6$H$_4$R$^8$;

R$^{14}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$;
—(CH$_2$)$_m$(CHR$^{61}$)$_s$OCONR$^{33}$R$^{75}$;  —(CH$_2$)$_m$(CHR$^{61}$)$_s$NR$^{20}$CONR$^{33}$R$^{82}$;
—(CH$_2$)$_q$(CHR$^{61}$)$_s$COOR$^{57}$;  —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$SOR$^{62}$; or —(CH$_2$)$_q$(CHR$^{61}$)$_s$C$_6$H$_4$R$^8$;

R$^{15}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$_{34}$;
—(CH$_2$)$_o$(CHR$^{61}$)$_s$OCONR$^{33}$R$^{75}$;  —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CH—R$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{16}$ is alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;  —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{17}$ is alkyl; alkenyl; —(CH$_2$)$_q$(CHR$^{61}$)$_s$OR$^{55}$; —(CH$_2$)(CHR$^{61}$)$_s$SR$^{56}$;
—(CH$_2$)$_q$(CHR$^{61}$)$_s$NR$^{33}$R$^{34}$;
—(CH$_2$)$_q$(CHR$^{61}$)$_s$ OCONR$^{33}$R$^{75}$;  —(CH$_2$)$_q$(CHR$^{61}$)$_s$NR$^{20}$CONR$^{33}$R$^{82}$;
—(CH$_2$)$_q$(CHR$^{61}$)$_s$COOR$^{57}$;  —(CH$_2$)$_q$(CHR$^{61}$)$_s$CONR$^{58}$R$^{59}$;
—(CH$_2$)$_q$(CHR$^{61}$)$_s$PO(OR$^{60}$)$_2$;
—(CH$_2$)$_q$(CHR$^{61}$)$_s$ SO$_2$R$^{62}$; or —(CH$_2$)$_q$(CHR$^{61}$)$_s$C$_6$H$_4$R$^8$;

R$^{18}$ is alkyl; alkenyl; —(CH$_2$)$_p$(CHR$^{61}$)$_s$OR$^{55}$; —(CH$_2$)$_p$(CHR$^{61}$)$_s$SR$^{56}$;
—(CH$_2$)$_p$(CHR$^{61}$)$_s$NR$^{33}$R$^{34}$;
—(CH$_2$)$_p$(CHR$^{61}$)$_s$OCONR$^{33}$R$^{75}$;  —(CH$_2$)$_p$(CHR$^{61}$)$_s$NR$^{20}$CONR$^{33}$R$^{82}$;
—(CH$_2$)$_p$(CHR$^{61}$)$_s$COOR$^{57}$;  —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^{19}$ is lower alkyl; —(CH$_2$)$_p$(CHR$^{61}$)$_s$OR$^{55}$; —(CH$_2$)$_p$(CHR$^{61}$)$_s$SR$^{56}$;
—(CH$_2$)$_p$(CHR$^{61}$)$_s$NR$^{33}$R$^{34}$;
—(CH$_2$)$_p$(CHR$^{61}$)$_s$OCONR$^{33}$R$^{75}$;  —(CH$_2$)$_p$(CHR$^{61}$)$_s$NR$^{20}$CONR$^{33}$R$^{82}$;
—(CH$_2$)$_p$(CHR$^{61}$)$_s$COOR$^{57}$;  —(CH$_2$)$_p$(CHR$^{61}$)$_s$CONR$^{58}$R$^{59}$;
—(CH$_2$)$_p$(CHR$^{61}$)$_s$PO(OR$^{60}$)$_2$;
—(CH$_2$)$_p$(CHR$^{61}$)$_s$SO$_2$R$^{62}$; or —(CH$_2$)$_o$(CHR$^{61}$)$_s$C$_6$H$_4$R$^8$; or R$^{18}$ and R$^{19}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{20}$ is H; alkyl; alkenyl; or aryl-lower alkyl;

R$^{21}$ is H; alkyl; alkenyl; —(CH$_2$)$_o$(CHR$^{61}$) OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;  —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$ SO$_2$R$^{62}$; or —(CH$_2$)$_o$(CHR$^{61}$)$_s$C$_6$H$_4$R$^8$;

R$^{22}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;  —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CH—R$^{61}$), SO$_2$R$^{62}$; or —(CH$_2$)$_o$(CHR$^{61}$)$_s$C$_6$H$_4$R$^8$;

R$^{23}$ is alkyl; alkenyl; —(CH$_2$)(CHR$^{61}$)OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;  —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)C$_6$H$_4$R$^8$;

R$^{24}$ is alkyl; alkenyl; —(CH$_2$)$_o$(CHR$^{61}$)$_s$OR$^{55}$; —(CH$_2$)$_o$(CHR$^{61}$)$_s$SR$^{56}$
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$;  —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$;  —(CH$_2$)$_o$(CHR$^{61}$)$_s$CONR$^{58}$R$^{59}$;

—$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{25}$ is H; alkyl; alkenyl; —$(CH_2)_m(CHR^{61})_s OR^{55}$;
—$(CH_2)_m (CHR^{61})_s SR^{56}$; $(CH_2)_m(CHR^{61})_s NR^{33}R^{34}$;
—$(CH_2)_m(CHR^{61})_s OCONR^{33}R^{75}$;
—$(CH_2)_m(CHR^{61})_s NR^{20}CONR^{33}R^{82}$; —$(CH_2)_o (CHR^{61})_s COOR^{57}$;
—$(CH_2)_o(CHR^{61})_s CONR^{58}R^{59}$; —$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{26}$ is H; alkyl; alkenyl; —$(CH_2)_m(CHR^{61})_s OR^{55}$; —$(C_2)_m(CHR^{61})_s SR^{56}$ $(CH_2)_m(CHR^{61})_s NR^{33}R^{34}$; —$(CH_2)_m(CHR^{61})_s OCONR^{33}R^{75}$;
—$(CH_2)_m(CHR^{61})_s NR^{20}CONR^{33}R^{82}$; —$(CH_2)_o(CHR^{61})_s COOR^{57}$;
—$(CH_2)_o(CHR^{61})_s CONR^{58}R^{59}$; —$(CH_2)_o(CHR^{61})_s PO(OR^{60})_2$;
—$(CH_2)_o(CHR^{61})_s SO_2R^{62}$; or —$(CH_2)_o(CH—R^{61})_s C_6H_4R^8$; or $R^{25}$ and $R^{26}$ taken together can form: —$(CH_2)_{2-6}$—;
—$(CH_2)_r O(CH_2)_r$—; —$(CH_2)_r S(CH_2)_r$—; or —$(CH_2)_r NR^{57}(CH_2)_r$—;

$R^{27}$ is H; alkyl; alkenyl; —$(CH_2)_o(CHR^{61})_s OR^{55}$, —$(CH_2)_o(CHR^{61})_s SR^{56}$;
—$(CH_2)_o(CHR^{61})_s NR^{33}R^{34}$;
—$(CH_2)_o(CHR^{61})_s COOR^{57}$; —$(CH_2)_o(CHR^{61})_s CONR^{58}R^{59}$;
—$(CH_2)_o(CHR^{61})_s OCONR^{33}R^{75}$;
—$(CH_2)_o(CHR^{61})_s NR^{20}CONR^{33}R^{82}$; —$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{28}$ is alkyl; alkenyl; —$(CH_2)_o(CHR^{61})_s$—$OR^{55}$; —$(C_2)_o(CHR^{61})_s SR^{56}$; —$(CH_2)_o(CHR^{61})_s NR^{33}R^{34}$
—$(CH_2)_o(CHR^{61})_s OCONR^{33}R^{75}$; —$(CH_2)_o(CHR^{61})_s NR^{20}CONR^{33}R^{82}$;
—$(CH_2)_o(CHR^{61})_s COOR^{57}$; —$(CH_2)_o(CHR^{61})_s CONR^{58}R^{59}$; —$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{29}$ is alkyl; alkenyl; —$(CH_2)_o(CHR^{61})_s OR^{55}$; —$(CH_2)_o(CHR^{61})_s SR^{56}$;
—$(CH_2)_o(CHR^{61})_s NR^{33}R^{34}$
—$(CH_2)_o(CHR^{61})_s OCONR^{33}R^{75}$; —$(CH_2)_o(CHR^{61})_s NR^{20}CONR^{33}R^{82}$;
—$(CH_2)_o(CHR^{61})_s COOR^{57}$; —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{30}$ is H; alkyl; alkenyl; or aryl-lower alkyl;

$R^{31}$ is H; alkyl; alkenyl; —$(CH_2)_p(CHR^{61})_s OR^{55}$; —$(CH_2)_p(CHR^{61})_s NR^{33}R^{34}$
—$(CH_2)_p(CHR^{61})_s OCONR^{33}R^{75}$; —$(CH_2)_p(CHR^{61})_s NR^{20}CONR^{33}R^{82}$;
—$(CH_2)_o(CHR^{61})_s COOR^{57}$; —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{32}$ is H; lower alkyl; or aryl-lower alkyl;

$R^{33}$ is H; alkyl, alkenyl; —$(CH_2)_m(CHR^{61})_s OR^{55}$; —$(CH_2)_m(CHR^{61})_s NR^{34}R^{63}$;
—$(CH_2)_m(CHR^{61})_s OCONR^{75}R^{82}$; —$(CH_2)_m(CHR^{61})_s NR^{20}CONR^{78}R^{82}$;

—$(CH_2)_o(CHR^{61})_s COR^{64}$; —$(CH_2)_o(CHR^{61})_s CONR^{58}R^{59}$,
—$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{34}$ is H; lower alkyl; aryl, or aryl-lower alkyl;

$R^{33}$ and $R^{34}$ taken together can form: —$(CH_2)_{2-6}$—;
—$(CH_2)_2 O(CH_2)_2$—; —$(CH_2)_2 S(CH_2)_2$—; or —$(CH_2)_2 NR^{57}(CH_2)_2$—;

$R^{35}$ is H; alkyl; alkenyl; —$(CH_2)_m(CHR^{61})_s OR^{55}$;
—$(CH_2)_m (CHR^{61})_s NR^{33}R^{34}$;
—$(CH_2)_m(CHR^{61})_s OCONR^{33}R^{75}$; —$(CH_2)_m(CHR^{61})_s NR^{20}CONR^{33}R^{82}$;
—$(CH_2)_p(CHR^{61})_s COOR^{57}$; —$(CH_2)_p(CHR^{61})_s CONR^{58}R^{59}$;
—$(CH_2)_p(CHR^{61})_s PO(OR^{60})_2$;
—$(CH_2)_p(CHR^{61})_s SO_2R^{62}$; or —$(CH_2)_p(CHR^{61})_s C_6H_4R^8$;

$R^{36}$ is H, alkyl; alkenyl; —$(CH_2)_o(CHR^{61})OR^{55}$; —$(CH_2)_p(CHR^{61})_s NR^{33}R^{34}$;
—$(CH_2)_p(CHR^{61})_s OCONR^{33}R^{75}$; —$(CH_2)_p(CHR^{61})_s NR^{20}CONR^{33}R^{82}$;
—$(CH_2)_p(CHR^{61})_s COOR^{57}$; —$(CH_2)_p(CHR^{61})_s CONR^{58}R^{59}$;
—$(CH_2)_p(CHR^{61})_s PO(OR^{60})_2$;
—$(CH_2)_p(CHR^{61})_s SO_2R^{62}$; or —$(CH_2)_o(CHR^{61})_s C_6H_4R^8$;

$R^{37}$ is H; F; Br; Cl; $NO_2$; $CF_3$; lower alkyl; —$(CH_2)_p(CHR^{61})_s OR^{55}$;
—$(CH_2)_p(CHR^{61})_s NR^{33}R^{34}$;
—$(CH_2)_p(CHR^{61})_s OCONR^{33}R^{75}$; —$(CH_2)_p(CHR^{61})_s NR^{20}CONR^{33}R^{82}$;
—$(CH_2)_o(CHR^{61})_s COOR^{57}$; —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{38}$ is H; F; Br; Cl; $NO_2$; $CF_3$; alkyl; alkenyl; —$(CH_2)_p(CHR^{61})_s OR^{55}$;
—$(CH_2)_p(CHR^{61})_s OCONR^{33}R^{75}$; —$(CH_2)_p(CHR^{61})_s NR^{20}CONR^{33}R^{82}$;
—$(CH_2)_o(CHR^{61})_s COOR^{57}$; —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2R^{62}$; or —$(CH_2)_o(CHR^{61})C_6H_4R^8$;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; $NO_2$; $CF_3$; alkyl; alkenyl; —$(CH_2)_p(CHR^{61})_s OR^{55}$;
—$(CH_2)_p(CHR^{61})_s OCONR^{33}R^{34}$;
—$(CH_2)_p(CHR^{61})_s OCONR^{33}R^{75}$; —$(CH_2)_p(CHR^{61})_s NR^{20}CONR^{33}R^{82}$;
—$(CH_2)_o(CHR^{61})_s COOR^{57}$; —$(CH_2)_o(CHR^{61})_s CONR^{58}R^{59}$;
—$(CH_2)_o(CHR^{61})_s PO(OR^{60})_2$;
—$(CH_2)_o(CHR^{61})_s SO_2R^{62}$; or —$(CH_2)_o(CHR^{61})_s C_6H_4R^8$;

$R^{42}$ is H; F; Br; Cl; $NO_2$; $CF_3$; alkyl; alkenyl; —$(CH_2)_p(CHR^{61})_s OR^{55}$;
—$(CH_2)_p(CHR^{61})_s NR^{33}R^{34}$;
—$(CH_2)_p(CHR^{61})_s OCONR^{33}R^{75}$; —$(CH_2)_p(CHR^{61})_s NR^{20}CONR^{33}R^{82}$;
—$(CH_2)_o(CHR^{61})_s COOR^{57}$; —$(CH_2)_o(CHR^{61})_s CONR^{58}R^{59}$;

—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{43}$ is H; alkyl; alkenyl; —(CH$_2$)$_m$(CHR$^{61}$)$_s$OR$^{55}$;
—(CH$_2$)$_m$ (CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$;
—(CH$_2$)$_o$(CHR$^{61}$)$_s$PO(OR$^{60}$)$_2$;
—(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{44}$ is alkyl; alkenyl; —(CH$_2$)$_r$(CHR$^{61}$)$_s$OR$^{55}$; —(CH$_2$)$_r$(CHR$^{61}$)$_s$SR$^{56}$;
—(CH$_2$)$_r$(CHR$^{61}$)$_s$NR$^{33}$R$^{34}$;
—(CH$_2$)$_r$(CHR$^{61}$)$_s$OCONR$^{33}$R$^{75}$; —(CH$_2$)$_r$(CHR$^{61}$)$_s$NR$^{20}$CONR$^{33}$R$^{82}$;
—(CH$_2$)$_r$(CHR$^{61}$)$_s$COOR$^{57}$; —(CH$_2$)$_r$(CHR$^{61}$)$_s$CONR$^{58}$R$^{59}$;
—(CH$_2$)$_r$(CHR$^{61}$)$_s$PO(OR$^{60}$)$_2$;
—(CH$_2$)$_r$(CHR$^{61}$)$_s$ SO$_2$R$^{62}$; or —(CH$_2$)$_r$(CHR$^{61}$)$_s$C$_6$H$_4$R$^8$;

R$^{45}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$;
—(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_s$(CHR$^{61}$)$_s$CONR$^{58}$R$^{59}$;
—(CH$_2$)$_s$(CHR$^{61}$)$_s$PO(OR$^{60}$)$_2$;
—(CH$_2$)$_s$(CHR$^{61}$)$_s$ SO$_2$R$^{62}$; or —(CH$_2$)$_s$(CHR$^{61}$)$_s$C$_6$H$_4$R$^8$;

R$^{46}$ is H; alkyl; alkenyl; or —(CH$_2$)$_o$(CHR$^{61}$)$_p$C$_6$H$_4$R$^8$;
R$^{47}$ is H; alkyl; alkenyl; or —(CH$_2$)$_o$(CH—R$^{61}$)$_s$OR$^{55}$;
R$^{48}$ is H; lower alkyl; lower alkenyl; or aryl-lower alkyl;
R$^{49}$ is H; alkyl; alkenyl; —(CHR$^{61}$)$_s$COOR$^{57}$; (CHR$^{61}$)$_s$CONR$^{58}$R$^{59}$; (CHR$^{61}$)$_s$PO(OR$^{60}$)$_2$;
—(CHR$^{61}$)$_s$SOR$^{62}$; or —(CHR$^{61}$)$_s$C$_6$H$_4$R$^8$;
R$^{50}$ is H; lower alkyl; or aryl-lower alkyl;
R$^{51}$ is H; alkyl; alkenyl; —(CH$_2$)$_m$(CHR$^{61}$)$_s$OR$^{55}$;
—(CH$_2$)$_m$ (CHR$^{61}$)$_s$SR$^{56}$;
—(CH$_2$)(CHR$^{61}$)$_s$NR$^{33}$R$^{34}$; —(CH$_2$)$_m$(CHR$^{61}$)OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$ COOR$^{57}$;
—(CH$_2$)$_o$(CHR$^{61}$)$_s$CONR$^{58}$R$^{59}$; —(CH$_2$)$_o$(CHR$^{61}$)$_p$PO(OR$^{60}$)$_2$;
—(CH$_2$)$_p$(CHR$^{61}$)$_s$ SO$_2$R$^{62}$; or —(CH$_2$)$_p$(CHR$^{61}$)$_s$C$_6$H$_4$R$^8$;

R$^{52}$ is H; alkyl; alkenyl; —(CH$_2$)$_m$(CHR$^{61}$)$_s$OR$^{55}$;
—(CH$_2$)$_m$ (CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$ COOR$^{57}$;
—(CH$_2$)$_o$(CHR$^{61}$)$_s$CONR$^{58}$R$^{59}$; —(CH$_2$)$_o$(CHR$^{61}$)$_p$PO(OR$^{60}$)$_2$;
—(CH$_2$)$_p$(CHR$^{61}$)$_s$ SO$_2$R$^{62}$; or —(CH$_2$)$_p$(CH—R$^{61}$)$_s$C$_6$H$_4$R$^8$;

R$^{53}$ is H; alkyl; alkenyl; —(CH$_2$)$_m$(CHR$^{61}$)$_s$OR$^{55}$;
—(CH$_2$)$_m$ (CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$ COOR$^{57}$;
—(CH$_2$)$_o$(CHR$^{61}$)$_s$CONR$^{58}$R$^{59}$; —(CH$_2$)$_o$(CHR$^{61}$)$_p$PO(OR$^{60}$)$_2$;
—(CH$_2$)$_p$(CHR$^{61}$)$_s$ SO$_2$R$^{62}$; or —(CH$_2$)$_p$(CHR$^{61}$)$_s$C$_6$H$_4$R$^8$;

R$^{54}$ is H; alkyl; alkenyl; —(CH$_2$)$_m$(CHR$^{61}$)$_s$OR$^{55}$;
—(CH$_2$)$_m$ (CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$; or —(CH$_2$)$_o$(CHR$^{61}$), C$_6$H$_4$R$^8$;

R$^{55}$ is H; lower alkyl; lower alkenyl; aryl-lower alkyl;
—(CH$_2$)$_m$(CHR$^{61}$)$_s$OR$^{57}$;
—(CH$_2$)$_m$(CHR$^{61}$)$_s$NR$^{34}$R$^{63}$; —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$; —(CH$_2$)$_o$(CHR$^{61}$)$_s$—COR$^{64}$;
—(CH$_2$)$_o$(CHR$^{61}$)COOR$^{57}$; or
—(CH$_2$)$_o$(CHR$^{61}$)$_s$CONR$^{58}$R$^{59}$;

R$^{56}$ is H; lower alkyl; lower alkenyl; aryl-lower alkyl;
—(CH$_2$)$_m$(CHR$^{61}$)$_s$OR$^{57}$;
—(CH$_2$)$_m$(CHR$^{61}$)$_s$NR$^{34}$R$^{63}$; —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; or
—(CH$_2$)$_o$(CHR$^{61}$)$_s$CONR$^{58}$R$^{59}$;

R$^{57}$ is H; lower alkyl; lower alkenyl; aryl lower alkyl; or heteroaryl lower alkyl;
R$^{58}$ is H; lower alkyl; lower alkenyl; aryl; heteroaryl; aryl-lower alkyl; or heteroaryl-lower alkyl;
R$^{59}$ is H; lower alkyl; lower alkenyl; aryl; heteroaryl; aryl-lower alkyl; or heteroaryl-lower alkyl; or
R$^{58}$ and R$^{59}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{60}$ is H; lower alkyl; lower alkenyl; aryl; or aryl-lower alkyl;
R$^{61}$ is H, alkyl; alkenyl; aryl; heteroaryl; aryl-lower alkyl; heteroaryl-lower alkyl; —(CH$_2$)$_p$OR$^{55}$;
—(CH$_2$)$_p$NR$^{33}$R$^{34}$; —(CH$_2$)$_p$OCONR$^{75}$R$^{82}$; —(CH$_2$)$_p$NR$^{20}$CONR$^{78}$R$^{82}$; —(CH$_2$)$_o$COOR$^{57}$; or —(CH$_2$)$_o$PO(COR$^{60}$)$_2$;

R$^{62}$ is lower alkyl; lower alkenyl; aryl, heteroaryl; or aryl-lower alkyl;
R$^{63}$ is H; lower alkyl; lower alkenyl; aryl, heteroaryl; aryl-lower alkyl; heteroaryl-lower alkyl;
—COR$^{64}$; —COOR$^{57}$; —CONR$^{58}$R$^{59}$; —SO$_2$R$^{62}$; or —PO(OR$^{60}$)$_2$;

R$^{34}$ and R$^{63}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{64}$ is H; lower alkyl; lower alkenyl; aryl; heteroaryl; aryl-lower alkyl; heteroaryl-lower alkyl; —(CH$_2$)$_p$(CHR$^{61}$)$_s$OR$^{65}$; —(CH$_2$)$_p$(CHR$^{61}$)$_s$SR$^{66}$; or —(CH$_2$)$_p$(CHR$^{61}$)$_s$NR$^{34}$R$^{63}$; —(CH$_2$)$_p$(CHR$^{61}$)OCONR$^{75}$R$^{82}$; —(CH$_2$)$_p$(CHR$^{61}$)$_s$NR$^{20}$CONR$^{78}$R$^{82}$;

R$^{65}$ is H; lower alkyl; lower alkenyl; aryl, aryl-lower alkyl; heteroaryl-lower alkyl; —COR$^{57}$; —COOR$^{57}$; or —CONR$^{58}$R$^{59}$;

R$^{66}$ is H; lower alkyl; lower alkenyl; aryl; aryl-lower alkyl; heteroaryl-lower alkyl; or —CONR$^{58}$R$^{59}$;

m is 2-4; o is 0-4; p is 1-4; q is 0-2; r is 1 or 2; s is 0 or 1;
R$^{67}$ being H; Cl; Br; F; NO$_2$; —NR$^{34}$COR$^{57}$; lower alkyl; or lower alkenyl;
R$^{68}$ being H; Cl; Br; F; NO$_2$; —NR$^{34}$COR$^{57}$; lower alkyl; or lower alkenyl;
R$^{69}$ being H; Cl; Br; F; NO$_2$; —NR$^{34}$COR$^{57}$; lower alkyl; or lower alkenyl; and
R$^{70}$ being H; Cl; Br; F; NO$_2$; —NR$^{34}$COR$^{57}$; lower alkyl; or lower alkenyl;

with the proviso that at least two of $R^{67}$, $R^{68}$, $R^{69}$ and $R^{70}$ are H; and Z is a chain of 12 α-amino acid residues, the positions of said amino acid residues in said chain being counted starting from the N-terminal amino acid, whereby these amino acid residues are, depending on their position in the chain, Gly or Pro, or of formula -A-CO—, or of formula —B—CO—, or of one of the types C: —NR$^{20}$CH(R$^{72}$)CO—;
D: —NR$^{20}$CH(R$^{73}$)CO—;
E: —NR$^{20}$CH(R$^{74}$)CO—;
F: —NR$^{20}$CH(R$^{84}$)CO—;
H: —NR$^{20}$—CH(CO—)—(CH$_2$)$_{4-7}$—CH(CO—)—NR$^{20}$—;
—NR$^{20}$—CH(CO—)—(CH$_2$)$_p$SS(CH$_2$)$_p$—CH(CO—)—NR$^{20}$—;
—NR$^{20}$—CH(CO—)—(—(CH$_2$)NR$^{20}$CO(CH$_2$)$_p$—CH(CO—)—NR$^{20}$—; and
—NR$^{20}$—CH(CO—)—(—(CH$_2$)$_p$NR$^{20}$CONR$^{20}$(CH$_2$)$_p$—CH(CO—)—NR$^{20}$—;

$R^{71}$ is H; lower alkyl; lower alkenyl; —(CX$_2$)$_p$(CHR$^{61}$)$_s$OR$^{75}$; —(CX$_2$)$_p$(CHR$^{61}$)$_s$SR$^{75}$;
—(CX$_2$)$_p$(CHR$^{61}$)$_s$NR$^{33}$R$^{34}$; —(CX$_2$)$_p$(CHR$^{61}$)$_s$OCONR$^{33}$R$^{75}$;
—(CX$_2$)$_p$(CHR$^{61}$)$_s$NR$^{20}$CONR$^{33}$R$^{82}$;
—(CX$_2$)$_o$(CHR$^{61}$)$_s$COOR$^{75}$; —(CX$_2$)$_p$CONR$^{58}$R$^{59}$;
—(CX$_2$)$_p$PO(OR$^{62}$)$_2$; —(CX$_2$)$_p$SO$_2$R$^{62}$; or
—(CX$_2$)$_o$—C$_6$R$^{67}$R$^{68}$R$^{69}$R$^{70}$R$^{76}$;

$R^{72}$ is H; lower alkyl; lower alkenyl; —(CX$_2$)$_p$(CHR$^{86}$)$_s$OR$^{85}$; or
—(CX$_2$)$_p$(CHR$^{86}$)$_s$SR$^{85}$;

$R^{73}$ is —(CX$_2$)$_o$R$^{77}$; —(CX$_2$)$_r$O(CH$_2$)$_o$R$^{77}$; —(CX$_2$)$_r$S(CH$_2$)$_o$R$^{77}$; or
—(CX$_2$)$_r$NR$^{20}$(CH$_2$)$_o$R$^{77}$;

$R^{74}$ is —(CX$_2$)$_p$NR$^{78}$R$^{79}$; —(CX$_2$)$_p$NR$^{77}$R$^{80}$; —(CX$_2$)$_p$C(=NR$^{80}$)NR$^{78}$R$^{79}$;
—(CX$_2$)$_p$C(=NOR$^{50}$)NR$^{78}$R$^{79}$;
—(CX$_2$)$_p$C(=NNR$^{78}$R$^{79}$)NR$^{78}$R$^{79}$; —(CX$_2$)$_p$NR$^{80}$C(=NR$^{80}$)NR$^{78}$R$^{79}$;
—(CX$_2$)$_p$N=C(NR$^{78}$R$^{80}$)NR$^{79}$R$^{80}$; —(CX$_2$)$_p$C$_6$H$_4$NR$^{78}$R$^{79}$; —(CX$_2$)$_p$C$_6$H$_4$NR$^{77}$R$^{80}$;
—(CX$_2$)$_p$C$_6$H$_4$C(=NR$^{80}$)NR$^{78}$R$^{79}$; —(CX$_2$)$_p$C$_6$H$_4$C(NOR$^{50}$)NR$^{78}$R$^{79}$;
—(CX$_2$)$_p$C$_6$H$_4$C(=NNR$^{78}$R$^{79}$)NR$^{78}$R$^{79}$; —(CX$_2$)$_p$C$_6$H$_4$NR$^{80}$C(=NR$^{80}$)NR$^{78}$R$^{79}$;
—(CX$_2$)$_p$C$_6$H$_4$N=C(NR$^{78}$R$^{80}$)NR$^{79}$R$^{80}$; —(CX$_2$)$_r$O(CX$_2$)$_m$NR$^{78}$R$^{79}$;
—(CX$_2$)$_r$O(CX$_2$)$_m$NR$^{77}$R$^{80}$;
—(CX$_2$)$_r$O(CX$_2$)$_p$C(=NR$^{80}$)NR$^{78}$R$^{79}$; —(CX$_2$)$_r$O(CX$_2$)$_p$ C(=NOR$^{50}$)NR$^{78}$R$^{79}$;
—(CX$_2$)$_r$O(CX$_2$)$_p$C(=NNR$^{78}$R$^{79}$)NR$^{78}$R$^{79}$; —(CX$_2$)$_r$O(CH$_2$)$_m$NR$^{80}$C(=NR$^{80}$)NR$^{78}$R$^{79}$;
—(CX$_2$)$_r$O(CX$_2$)$_m$N=C(NR$^{78}$R$^{80}$)NR$^{79}$R$^{80}$; —(CX$_2$)$_s$O(CX$_2$)$_p$C$_6$H$_4$CHR$^{78}$R$^{79}$;
—(CX$_2$)$_r$O(CX$_2$)$_p$C$_6$H$_4$C(=NR$^{80}$)NR$^{78}$R$^{79}$; —(CX$_2$)$_r$O(CX$_2$)$_p$C$_6$H$_4$C(=NOR$^{50}$)NR$^{78}$R$^{79}$
—(CX$_2$)$_r$O(CX$_2$)$_p$C$_6$H$_4$C(=NNR$^{78}$R$^{79}$)NR$^{78}$R$^{79}$;
—(CX$_2$)$_r$O(CX$_2$)$_p$C$_6$H$_4$NR$^{80}$C(=NR$^{80}$)NR$^{78}$R$^{79}$;
—(CX$_2$)$_r$S(CX$_2$)$_m$NR$^{78}$R$^{79}$;
—(CX$_2$)$_r$S(CX$_2$)$_m$NR$^{77}$R$^{80}$; —(CX$_2$)$_r$S(CX$_2$)$_p$C(NR$^{80}$)NR$^{78}$R$^{79}$;
—(CX$_2$)$_r$S(CX$_2$)$_p$C(=NOR$^{50}$)NR$^{78}$R$^{79}$; —(CX$_2$)$_r$S(CX$_2$)$_p$C(=NNR$^{78}$R$^{79}$)NR$^{78}$R$^{79}$;
—(CX$_2$)$_r$S(CX$_2$)$_m$NR$^{80}$C(=NR$^{80}$)NR$^{78}$R$^{79}$; —(CX$_2$)$_r$S(CX$_2$)$_m$N=C(NR$^{78}$R$^{80}$)NR$^{79}$R$^{80}$;
—(CX$_2$)$_r$S(CX$_2$)$_p$C$_6$H$_4$CHR$^{78}$R$^{79}$; —(CX$_2$)$_r$S(CX$_2$)$_p$C$_6$H$_4$C(=NR$^{80}$)NR$^{78}$R$^{79}$;
—(CX$_2$)$_r$S(CX$_2$)$_p$C$_6$H$_4$C(=NR$^{50}$)NR$^{78}$R$^{79}$;
—(CX$_2$)$_r$S(CX$_2$)$_p$C$_6$H$_4$C(=NNR$^{78}$R$^{79}$)NR$^{78}$R$^{79}$;
—(CX$_2$)$_r$S(CX$_2$)$_p$C$_6$H$_4$NR$^{80}$C(=NR$^{80}$)NR$^{78}$R$^{79}$;
—(CX$_2$)$_p$NR$^{80}$COR$^{64}$;
—(CX$_2$)$_p$NR$^{80}$COR$^{77}$;
—(CX$_2$)$_p$NR$^{80}$CONR$^{78}$R$^{79}$; —(CX$_2$)$_p$C$_6$H$_4$NR$^{80}$CONR$^{78}$R$^{79}$ or —(CX$_2$)NR$^{20}$CO—[(CX$_2$)$_u$—XX]$_t$—CH$_3$ where XX is —O—; —NR$^{20}$—, or —S—; u is 1-3, and t is 1-6;

$R^{75}$ is lower alkyl; lower alkenyl; or aryl-lower alkyl;

$R^{33}$ and $R^{75}$ taken together can form: —(CX$_2$)$_{2-6}$—; —(CX$_2$)$_2$O(CX$_2$)$_2$—; —(CX$_2$)$_2$S(CX$_2$)$_2$—; or $R^{75}$ and $R^{82}$ taken together can form: —(CX$_2$)$_{2-6}$—; —(CX$_2$)$_2$O(CX$_2$)$_2$—; —(CX$_2$)$_2$S(CX$_2$)$_2$—; or —(CX$_2$)$_2$NR$^{57}$(CX$_2$)$_2$—;

$R^{76}$ is H; lower alkyl; lower alkenyl; aryl-lower alkyl; —(CX$_2$)$_o$OR$^{72}$; —(CX$_2$)$_o$SR$^{72}$;
—(CX$_2$)$_o$NR$^{33}$R$^{34}$; —(CX$_2$)$_o$OCONR$^{33}$R$^{75}$; —(CX$_2$)$_o$NR$^{20}$CONR$^{33}$R$^{82}$;
—(CX$_2$)$_o$COOR$^{75}$; —(CX$_2$)$_o$CONR$^{58}$R$^{59}$; —(CX$_2$)$_o$PO(OR$^{60}$)$_2$; —(CX$_2$)$_p$SO$_2$R$^{62}$; or
—(CX$_2$)$_o$COR$^{64}$;

$R^{77}$ is —C$_6$R$^{67}$R$^{68}$R$^{69}$R$^{70}$R$^{76}$; or a heteroaryl group of one of the formulae

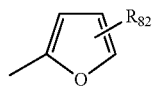

H1

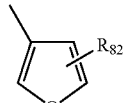

H2

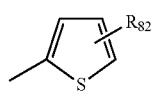

H3

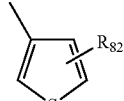

H4

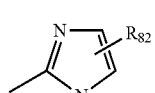

H5

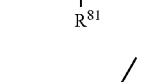

H6

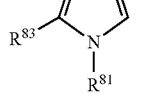

H7

-continued
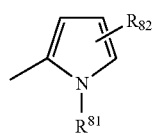
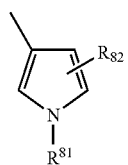
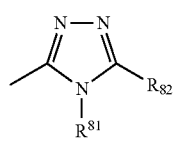
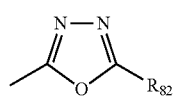
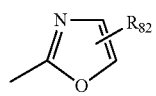
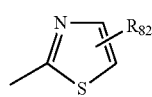
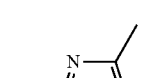
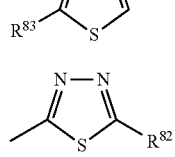
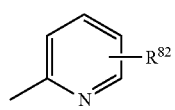
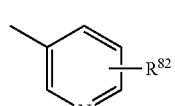
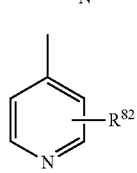
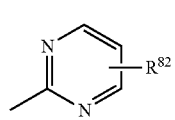
H8
H9
H10
H11
H12
H13
H14
H15
H16
H17
H18
H19
H20
-continued
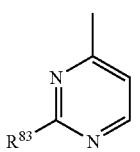
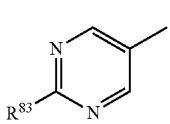
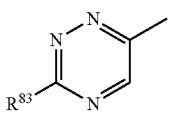
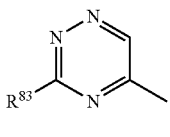
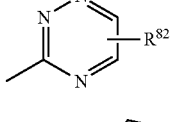
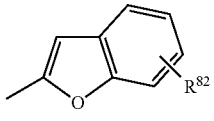
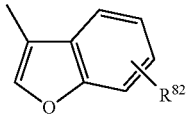
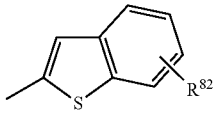
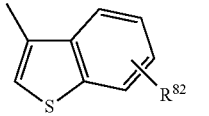
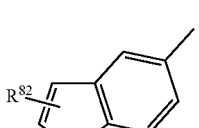
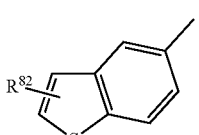
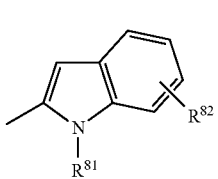
H21
H22
H23
H24
H25
H26
H27
H28
H29
H30
H31
H32

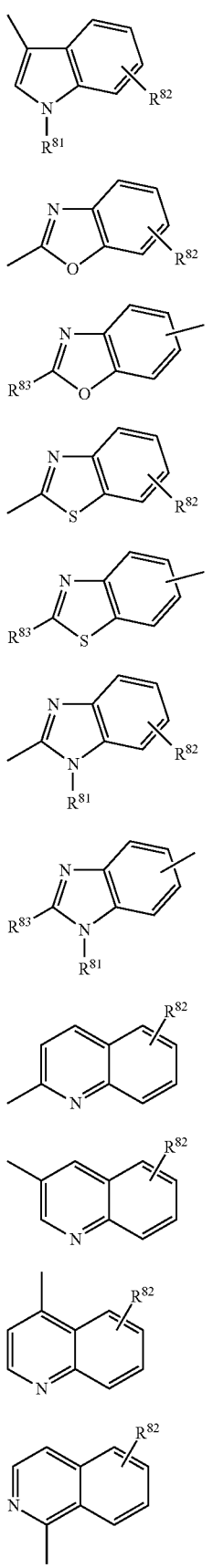
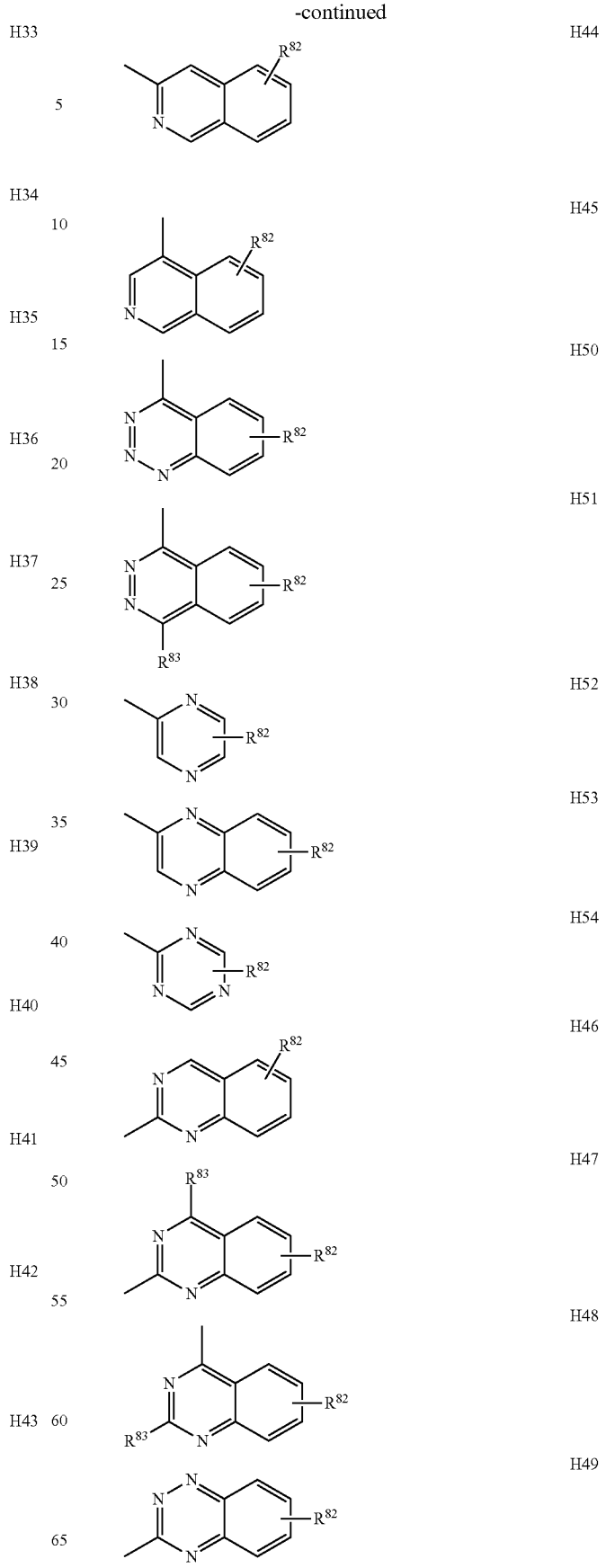

R$^{78}$ is H; lower alkyl; aryl; or aryl-lower alkyl;
R$^{78}$ and R$^{82}$ taken together can form: —(CX$_2$)$_{2-6}$—; —(CX$_2$)$_2$O(CX$_2$)$_2$—; —(CX$_2$)$_2$S(CX$_2$)$_2$—; or —(CX$_2$)$_2$NR$^{57}$(CX$_2$)$_2$—;
R$^{79}$ is H; lower alkyl; aryl; or aryl-lower alkyl; or
R$^{78}$ and R$^{79}$, taken together, can be —(CX$_2$)$_{2-7}$—; —(CX$_2$)$_2$O(CX$_2$)$_2$—; or —(CX$_2$)$_2$NR$^{57}$(CX$_2$)$_2$—;
R$^{80}$ is H; or lower alkyl;
R$^{81}$ is H; lower alkyl; or aryl-lower alkyl;
R$^{82}$ is H; lower alkyl; aryl; heteroaryl; or aryl-lower alkyl;
R$^{33}$ and R$^{82}$ taken together can form: —(CX$_2$)$_{2-6}$—; —(CX$_2$)$_2$O(CX$_2$)$_2$—; —(CX$_2$)$_2$S(CX$_2$)$_2$—; or —(CX$_2$)$_2$NR$^{57}$(CX$_2$)$_2$—;
R$^{83}$ is H; lower alkyl; aryl; or —NR$^{78}$R$^{79}$;
R$^{84}$ is —(CX$_2$)$_m$(CHR$^{61}$)$_s$OH; —(CX$_2$)$_p$CONR$^{78}$R$^{79}$; —(CX$_2$)$_p$NR$^{80}$CONR$^{78}$R$^{79}$; —(CX$_2$)$_p$C$_6$H$_4$CONR$^{78}$R$^{79}$; or —(CX$_2$)$_p$C$_6$H$_4$NR$^{80}$CONR$^{78}$R$^{79}$;
R$^{85}$ is lower alkyl; or lower alkenyl;
R$^{86}$ is H, alkyl; alkenyl; —(CX$_2$)$_p$OR$^{85}$; —(CX$_2$)$_p$SR$^{85}$
R$^{87}$ is H; alkyl; alkenyl; heteroaryl, aryl-lower alkyl; —(CX$_2$)$_p$OR$^{55}$; —(CX$_2$)$_p$OCONR$^{75}$R$^{82}$; —(CX$_2$)$_p$NR$^{20}$CONR$^{78}$R$^{82}$; —(CX$_2$)$_p$COOR$^{57}$, or —(CX$_2$)$_p$PO(OR$^{60}$)$_2$;
X is H; or optionally halogen;
with the proviso that in said chain of 12 α-amino acid residues Z the amino acid residues in positions 1 to 12 are, in a preferred embodiment:
P1: of type C or of type D or of type E or of type F, or the residue is Pro;
P2: of type D or of type E;
P3: of type C or of type D, or the residue is Gly or Pro;
P4: of type C or of type E or of type F, or the residue is Gly or Pro;
P5: of type E or of type D or of type C, or the residue is Gly or Pro;
P6: of type E or of type F or of type C or of formula -A-CO—, or the residue is Gly or Pro;
P7: of type C or of type E or of type F or of formula —B—CO—;
P8: of type D or of type C, or of Type F, or the residue is Pro;
P9: of type C or of type E or of type D or of type F;
P10: of type E;
P11: of type C or of type F, or the residue is Pro or Gly; and
P12: of type C or of type D or of type E or of type F, or the residue is Pro; or
P4 and P9 and/or P2 and P11, taken together, can form a group of type H; and
at P6, P10 and P11 also D-isomers being possible;
or, alternatively, but in a less preferred embodiment:
P1: of type C or of type D or of type E or of type F, or the residue is Pro;
P2: of type C or of type F, or the residue is Pro or Gly;
P3: of type E;
P4: of type C or of type E or of type D or of type F;
P5: of type D or of type C, or of type F, or the residue is Pro;
P6: of type C or of type E or of type F or of formula —B—CO—;
P7: of type E or of type F or of type C or of formula -A-CO—, or the residue is Gly or Pro;
P8: of type E or of type D or of type C, or the residue is Gly or Pro;
P9: of type C or of type E or of type F; or the residue is Gly or Pro;
P10: of type C or of type D, or the residue is Gly or Pro;
P11: of type D or of type E; and
P12: of type C or of type D or of type E or of type F, or the residue is Pro; or
P4 and P9 and/or P2 and P11, taken together, can form a group of type H; and
at P2, P3, and P7 also D-isomers being possible;
and pharmaceutically acceptable salts thereof.

In accordance with the present invention these β-hairpin peptidomimetics can be prepared by a process which comprises
(a) coupling an appropriately functionalized solid support with an appropriately N-protected derivative of that amino acid which in the desired end-product is in position 5, 6 or 7, any functional group which may be present in said N-protected amino acid derivative being likewise appropriately protected;
(b) removing the N-protecting group from the product thus obtained;
(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;
(d) removing the N-protecting group from the product thus obtained;
(e) repeating steps (c) and (d) until the N-terminal amino acid residue has been introduced;
(f) coupling the product thus obtained with a compound of the general formula

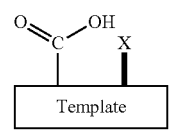

II wherein

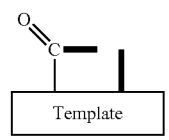

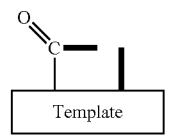

is as defined above and X is an N-protecting group or, if is to be group (a1) or (a2), above, alternatively
(fa) coupling the product obtained in step (e) with an appropriately N-protected derivative of an amino acid of the general formula

HOOC—B—H    III or

HOOC-A-H    IV wherein B and A are as defined above, any functional group which may be present in said N-protected amino acid derivative being likewise appropriately protected;

(fb) removing the N-protecting group from the product thus obtained; and (fc) coupling the product thus obtained with an appropriately N-protected derivative of an amino acid of the above general formula IV and, respectively, III, any functional group which may be present in said N-protected amino acid derivative being likewise appropriately protected;

(g) removing the N-protecting group from the product obtained in step (f) or (fc);

(h) coupling the product thus obtained with an appropriately N-protected derivative of that amino acid which in the desired end-product is in position 12, any functional group which may be present in said N-protected amino acid derivative being likewise appropriately protected;

(i) removing the N-protecting group from the product thus obtained;

(j) coupling the product thus obtained with an appropriately N-protected derivative of that amino acid which in the desired end-product is one position farther away from position 12, any functional group which may be present in said N-protected amino acid derivative being likewise appropriately protected;

(k) removing the N-protecting group from the product thus obtained;

(l) repeating steps (j) and (k) until all amino acid residues have been introduced;

(m) if desired, selectively deprotecting one or several protected functional group(s) present in the molecule and appropriately substituting the reactive group(s) thus liberated;

(o) detaching the product thus obtained from the solid support;

(p) cyclizing the product cleaved from the solid support;

(q) if desired, forming one or two interstrand linkage(s) between side-chains of appropriate amino acid residues at opposite positions of the β-strand region;

(r) removing any protecting groups present on functional groups of any members of the chain of amino acid residues and, if desired, any protecting group(s) which may in addition be present in the molecule; and (s) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

Alternatively, the peptidomimetics of the present invention can be prepared by (a') coupling an appropriately functionalized solid support with a compound of the general formula

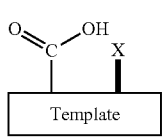

II wherein

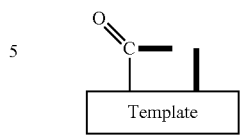

is as defined above and X is an N-protecting group or, if

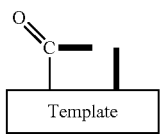

is to be group (a1) or (a2), above, alternatively (a'a) coupling said appropriately functionalized solid support with an appropriately N-protected derivative of an amino acid of the general formula

HOOC—B—H                                III or

HOOC-A-H                                 IV wherein B and A are as defined above, any functional group which may be present in said N-protected amino acid derivative being likewise appropriately protected;

(a'b) removing the N-protecting group from the product thus obtained; and (a'c) coupling the product thus obtained with an appropriately N-protected derivative of an amino acid of the above general formula IV and, respectively, III, any functional group which may be present in said N-protected amino acid derivative being likewise appropriately protected;

(b') removing the N-protecting group from the product obtained in step (a') or (a'c);

(c') coupling the product thus obtained with an appropriately N-protected derivative of that amino acid which in the desired end-product is in position 12, any functional group which may be present in said N-protected amino acid derivative being likewise appropriately protected;

(d') removing the N-protecting group from the product thus obtained;

(e') coupling the product thus obtained with an appropriately N-protected derivative of that amino acid which in the desired end-product is one position farther away from position 12, any functional group which may be present in said N-protected amino acid derivative being likewise appropriately protected;

(f) removing the N-protecting group from the product thus obtained;

(g') repeating steps (e') and (f) until all amino acid residues have been introduced;

(h') if desired, selectively deprotecting one or several protected functional group(s) present in the molecule and appropriately substituting the reactive group(s) thus liberated;

(i') detaching the product thus obtained from the solid support;

(j') cyclizing the product cleaved from the solid support;

(k') if desired forming one or two interstrand linkage(s) between side-chains of appropriate amino acid residues at opposite positions of the β-strand region;

(l') removing any protecting groups present on functional groups of any members of the chain of amino acid residues and, if desired, any protecting group(s) which may in addition be present in the molecule; and (m') if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

The peptidomimetics of the present invention can also be enantiomers of the compounds of formula I. These enantiomers can be prepared by a modification of the above processes in which enantiomers of all chiral starting materials are used.

As used in this description, the term "alkyl", taken alone or in combinations, designates saturated, straight-chain or branched hydrocarbon radicals having up to 24, preferably up to 12, carbon atoms, optionally substituted with halogen. Similarly, the term "alkenyl" designates straight chain or branched hydrocarbon radicals having up to 24, preferably up to 12, carbon atoms and containing at least one or, depending on the chain length, up to four olefinic double bonds, optionally substituted with halogen. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element -A-CO— designates amino acid building blocks which in combination with the structural element —B—CO— form templates (a1) and (a2). Templates (a) through (p) constitute building blocks which have an N-terminus and a C-terminus oriented in space in such a way that the distance between those two groups may lie between 4.0-5.5 A. A peptide chain Z is linked to the C-terminus and the N-terminus of the templates (a) through (p) via the corresponding N- and C-termini so that the template and the chain form a cyclic structure such as that depicted in formula I. In a case as here where the distance between the N- and C-termini of the template lies between 4.0-5.5 A the template will induce the H-bond network necessary for the formation of a β-hairpin conformation in the peptide chain Z. Thus template and peptide chain form a β-hairpin mimetic.

The β-hairpin conformation is highly relevant for the anti-bacterial activity of the β-hairpin mimetics of the present invention. The β-hairpin stabilizing conformational properties of the templates (a) through (p) play a key role not only for the selective antibacterial activity but also for the synthetic processes defined hereinabove, as incorporation of the templates at the beginning or near the middle of the linear protected peptide precursors enhances cyclization yields significantly.

Building blocks A1-A69 belong to a class of amino acids wherein the N-terminus is a secondary amine forming part of a ring. Among the genetically encoded amino acids only proline falls into this class. The configuration of building block A1 through A69 is (D), and they are combined with a building block —B—CO— of (L)-configuration. Preferred combinations for templates (a1) are -$^D$A1-CO—$^L$B—CO— to $^D$A69-CO—$^L$B—CO—. Thus, for example, $^D$Pro-$^L$Pro constitutes the prototype of templates (a1). Less preferred, but possible are combinations -$^L$A1-CO—$^D$B—CO— to $^L$A69-CO—$^D$B—CO— forming templates (a2). Thus, for example, $^L$Pro-$^D$Pro constitutes the prototype of template (a2).

It will be appreciated that building blocks -A1-CO— to -A69-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1-A69 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$ building blocks -A1-CO— to -A69-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

—$R^2$: H; lower alkyl; lower alkenyl; $(CH_2)_m OR^{55}$ (where $R^{55}$: lower alkyl; or lower alkenyl); $(CH_2)_m SR^{56}$ (where $R^{56}$: lower alkyl; or lower alkenyl); $(CH_2)_m NR^{33}R^{34}$ (where $R^{33}$: lower alkyl; or lower alkenyl; $R^{34}$: H; or lower alkyl; $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; $R^{57}$: H; or lower alkyl); $(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_o N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2 R^{62}$ (where $R^{62}$: lower alkyl; or lower alkenyl); or —$(CH_2)_q C_6 H_4 R^8$ (where $R^8$: H; F; Cl; $CF_3$; lower alkyl; lower alkenyl; or lower alkoxy).

—$R^3$: H; lower alkyl; lower alkenyl; —$(CH_2)_m OR^{55}$ (where $R^{55}$: lower alkyl; or lower alkenyl); —$(CH_2)_m SR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2 O(CH_2)_2$—; —$(CH_2)_2 S(CH_2)_2$—; or —$(CH_2)_2 NR^{57}(CH_2)_2$—; where $R^{57}$: H; or lower alkyl); —$(CH_2)_m OCONR^{33}R^{75}$ (where $R^{33}$: H; or lower alkyl; or lower alkenyl; $R^{75}$:

lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$—; where $R^{57}$: H; or lower alkyl); $(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^4$: H; lower alkyl; lower alkenyl; —$(CH_2)_m OR^{55}$ (where $R^{55}$: lower alkyl; or lower alkenyl); —$(CH_2)_m SR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^5$: lower alkyl; lower alkenyl; —$(CH_2)_o R^{55}$ (where $R^{55}$: lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: where H; or lower alkyl); $(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_o N(R^{20})COR^{64}$ (where: $R^{20}$: H; or lower alkyl; $R^{64}$: alkyl; alkenyl; aryl; and aryl-lower alkyl; heteroaryl-lower alkyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^6$: H; lower alkyl; lower alkenyl; —$(CH_2)_o OR^{55}$ (where $R^{55}$: lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^7$: lower alkyl; lower alkenyl; —$(CH_2)_q OR^{55}$ (where $R^{55}$: lower alkyl; or lower alkenyl); —$(CH_2)_q SR^{56}$ (where $R^{56}$: lower alkyl; or lower alkenyl); —$(CH_2)_q NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_q OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_q NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_q N(R^{20})COR^{64}$ (where: $R^{20}$: H; or lower alkyl; $R^{64}$:

lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); (CH$_2$)$_s$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^8$: H; F; Cl; CF$_3$; lower alkyl; lower alkenyl; —(CH$_2$)$_o$OR$^{55}$ (where R$^{55}$: lower alkyl; or lower alkenyl); (CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^9$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{10}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{11}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{12}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl);

—$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m N(R^{20})COR^{64}$ (where: $R^{20}$: H; or lower alkyl; $R^{64}$: lower alkyl; or lower alkenyl); —$(CH_2)_s COOR^{57}$ (where $R^{57}$: lower alkyl; or lower alkenyl); —$(CH_2)_t CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_r PO(OR^{60})_2$ (where $R^{60}$: lower alkyl; or lower alkenyl); —$(CH_2)_s SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^{13}$: lower alkyl; lower alkenyl; —$(CH_2)_q OR^{55}$ (where $R^{55}$: lower alkyl; or lower alkenyl); —$(CH_2)_q SR^{56}$ (where $R^{56}$: lower alkyl; or lower alkenyl); —$(CH_2)_q NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_q OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR(CH_2)_2$—; where $R^{57}$: H; or lower alkyl); —$(CH_2)_q NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_q N(R^{20})COR^{64}$ (where: $R^{20}$: H; or lower alkyl; $R^{64}$: lower alkyl; or lower alkenyl); —$(CH_2)_r COO^{57}$ (where $R^{57}$: lower alkyl; or lower alkenyl); —$(CH_2)_q CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_r PO(OR^{60})_2$ (where $R^{60}$: lower alkyl; or lower alkenyl); —$(CH_2)_s SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^{14}$: H; lower alkyl; lower alkenyl; —$(CH_2)_m OR^{55}$ (where $R^{55}$: lower alkyl; or lower alkenyl); —$(CH_2)_m SR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m N(R^{20})COR^{64}$ (where: $R^{20}$: H; lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); —$(CH_2)_q C_6H_4R^8$ (where $R^8$: H; F; Cl; $CF_3$; lower alkyl; lower alkenyl; or lower alkoxy).

$R^{15}$: lower alkyl; lower alkenyl; —$(CH_2)_o OR^{55}$ (where $R^{55}$: lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_o N(R^{20})COR^{64}$ (where: $R^{20}$: H; or lower alkyl; $R^{64}$: lower alkyl; or lower alkenyl); particularly favoured are $NR^{20}CO$ lower alkyl ($R^{20}$=H; or lower alkyl); —$(CH_2)_o COOR^{57}$ (where $R^{57}$: lower alkyl; or lower alkenyl); —$(CH_2)_o CONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO_o(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^{16}$: lower alkyl; lower alkenyl; —$(CH_2)_o OR^{55}$ (where $R^{55}$: lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —(CH$_2$)$_2$NR$^{57}$(CH$_2$)$_2$—; where R$^{57}$: H; or lower alkyl);
—(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl);
—(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{17}$: lower alkyl; lower alkenyl; —(CH$_2$)$_q$OR$^{55}$ (where R$^{55}$: lower alkyl; or lower alkenyl); —(CH$_2$)$_q$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);
—(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl);
—(CH$_2$)$_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$N(R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 the following are preferred: A5 with R$^2$ being H, A8, A22, A25, A38 with R$^2$ being H, A42, A47, and A50. Most preferred are building blocks of type A8':

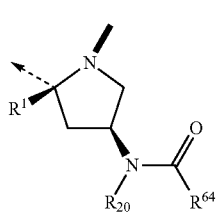

A8' wherein R$^{20}$ is H or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl)benzyl (A8'-3); diphenylmethyl (A8'-4); 3-aminopropyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, Biopolymers, 1968, 6, 1425-1434; W. Kabsch, C Sander, Biopolymers 1983, 22, 2577). Such building blocks or templates are ideally suited for the stabilization of (β-hairpin conformations in peptide loops (D. Obrecht, M. Altorfer, J. A. Robinson, "Novel Peptide Mimetic Building Blocks and Strategies for Efficient Lead Finding", Adv. Med. Chem. 1999, Vol. 4, 1-68; P. Balaram, "Non-standard amino acids in peptide design and protein engineering", Curr. Opin. Struct. Biol. 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", Biopolymers 1995, 35, 1-9; V. J. Hruby, F. Al-Obeidi, W. Kazmierski, Biochem. J. 1990, 268, 249-262).

It has been shown that both enantiomers of building blocks -A70-CO— to A104-CO— in combination with a building block —B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", Adv. Med. Chem. 1999, Vol. 4, 1-68; D. Obrecht, C. Spiegler, P. Schönholzer, K. Müller, H. Heimgartner, F. Stierli, Helv. Chim. Acta 1992, 75, 1666-1696; D. Obrecht, U. Bohdal, J. Daly, C. Lehmann, P. Schünholzer, K. Müller, Tetrahedron 1995, 51, 10883-10900; D. Obrecht, C. Lehmann, C. Ruffieux, P. Schünholzer, K. Müller, Helv. Chim. Acta 1995, 78, 1567-1587; D. Obrecht, U. Bohdal, C. Broger, D. Bur, C. Lehmann, R. Ruffieux, P. Schünholzer, C. Spiegler, Helv. Chim. Acta 1995, 78, 563-580; D. Obrecht, H. Karajiannis, C. Lehmann, P. Schünholzer, C. Spiegler, Helv. Chim. Acta 1995, 78, 703-714).

Thus, for the purposes of the present invention templates (a1) can also consist of -A70-CO— to A104-CO— where building block A70 to A104 is of either (D)- or (L)-configuration, in combination with a building block —B—CO— of (L)-configuration.

Preferred values for R$^{20}$ in A70 to A104 are H or lower alkyl with methyl being most preferred. Preferred values for R$^{18}$, R$^{19}$ and R$^{21}$-R$^{29}$ in building blocks A70 to A104 are the following:
R$^{18}$: lower alkyl.
R$^{19}$: lower alkyl; lower alkenyl; —(CH$_2$)$_p$OR$^{55}$ (where R$^{55}$: lower alkyl; or lower alkenyl); —(CH$_2$)$_p$SR$^{56}$ (where R$^{56}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);
—(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$N(R$^{20}$)COR$^{64}$ (where: R$^{20}$: H; or lower alkyl; R$^{64}$: lower alkyl; or lower alkenyl); —(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$PO(OR$^{60}$)$_2$ (where R$^{60}$: lower alkyl; or lower alkenyl); —(CH$_2$)$_p$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{21}$: H; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{15}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); (CH$_2$)$_o$SO$_2$R$^{62}$ (where R$^{62}$: lower alkyl; or lower alkenyl); or (CH$_2$)$_q$C$_6$H$_4$R$^8$ (where R$^8$: H; F; Cl; CF$_3$; lower alkyl; lower alkenyl; or lower alkoxy).

R$^{22}$: lower alkyl; lower alkenyl; —(CH$_2$)$_o$OR$^{15}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF; lower alkyl; lower alkenyl; or lower alkoxy).

R$^{23}$: H; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$) NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); particularly favoured are NR$^{20}$CO lower alkyl (R$^{20}$=H; or lower alkyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy);

R$^{24}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); particularly favoured are $NR^{20}CO$ lower alkyl ($R^{20}$=H; or lower alkyl); —$(CH_2)_o$ $COOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy);

$R^{25}$: H; lower alkyl; lower alkenyl; —$(CH_2)_mOR^{55}$ (where $R^{55}$: lower alkyl; or lower alkenyl); —$(CH_2)_m$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{26}$: H; lower alkyl; lower alkenyl; —$(CH_2)_mOR^{55}$ (where $R^{55}$: lower alkyl; or lower alkenyl); —$(CH_2)_m$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(H_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

Alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{27}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCON^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); —$(CH_2)_o$ $PO(OR^{60})_2$ (where $R^{60}$: lower alkyl; or lower alkenyl); —$(CH_2)_sSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{28}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); —$(CH_2)_o$ $PO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{29}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favored are $NR^{20}CO$ lower-alkyl ($R^{20}$=H; or lower alkyl); —$(CH_2)_o$ $COOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

For templates (b) to (p), such as (b1) and (c1), the preferred values for the various symbols are the following:
$R^8$: H; F; Cl; $CF_3$; lower alkyl; lower alkenyl; —$(CH_2)_o$ $OR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2$ $O(CH_2)_2$—; —$(CH_2)_2S(CH_2)_2$—; or —$(CH_2)_2NR^{57}$ $(CH_2)_2$—; where $R^{57}$: H; or lower alkyl); —$(CH_2)_o$ $OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).
$R^{20}$: H; or lower alkyl.
$R^{30}$: H, methyl.

$R^{31}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2$ $S(CH_2)_2$—; or
—$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); (—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_sC_6H_4R^8$ (where $R^8$: H; F; Cl; $CF_3$; lower alkyl; lower alkenyl; or lower alkoxy); most preferred is —$CH_2CONR^{58}R^{59}$ ($R^{58}$: H; or lower alkyl; $R^{59}$: lower alkyl; or lower alkenyl).
$R^{32}$: H, methyl.
$R^{33}$: lower alkyl; lower alkenyl; —$(CH_2)_mOR^{55}$ (where $R^{8S}$: lower alkyl; or lower alkenyl); —$(CH_2)_mNR^{34}R^{63}$ (where $R^{34}$: lower alkyl; or lower alkenyl; $R^{63}$: H; or lower alkyl; or $R^{34}$ and $R^{63}$ taken together form:
—$(CH_2)_{2-6}$—; —$(CH_2)_2O(CH_2)_2$—; —$(CH_2)_2$ $S(CH_2)_2$—; or
—$(CH_2)_2NR^{57}(CH_2)_2$—; where $R^{57}$: H; or lower alkyl); $(CH_2)_mOCONR^{75}R^{82}$ (where $R^{75}$: lower alkyl; or lower alkenyl; $R^{82}$: H; or lower alkyl; or $R^{75}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mNR^{20}CONR^{78}R^{82}$ (where $R^{20}$: H; or lower lower alkyl; $R^{78}$: H; or lower alkyl; or lower alkenyl; $R^{82}$: H; or lower alkyl; or $R^{78}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).
$R^{34}$: H; or lower alkyl.
$R^{35}$: H; lower alkyl; lower alkenyl; —$(CH_2)_mOR^{55}$ (where $R^{55}$: lower alkyl; or lower alkenyl); —$(CH_2)_m$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S$ $(CH_2)_2$—; or
—$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).
$R^{36}$: lower alkyl; lower alkenyl; or aryl-lower alkyl.
$R^{37}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl);
—$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).
$R^{38}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl);
—$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).
$R^{39}$: H; lower alkyl; lower alkenyl; —$(CH_2)_mOR^{55}$ (where $R^{55}$: lower alkyl; or lower alkenyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).
$R^{40}$: lower alkyl; lower alkenyl; or aryl-lower alkyl.
$R^{41}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl);
—$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)N(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where R: H; F; Cl; $CF_3$; lower alkyl; lower alkenyl; or lower alkoxy).
$R^{42}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl);
—$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{43}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{44}$: lower alkyl; lower alkenyl; —$(CH_2)_pOR^{55}$ (where $R^{55}$: lower alkyl; or lower alkenyl); —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_oC_6H_4R^8$ (where $R^8$: H; F; Cl; $CF_3$; lower alkyl; lower alkenyl; or lower alkoxy).

$R^{45}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^7$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{46}$: H; lower alkyl; lower alkenyl; —$(CH_2)_sOR^{55}$ (where $R^{55}$: lower alkyl; or lower alkenyl); —$(CH_2)_sSR^{56}$ (where $R^{56}$: lower alkyl; or lower alkenyl); —$(CH_2)_sNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{47}$: H; or $OR^{55}$ (where $R^{55}$: lower alkyl; or lower alkenyl).

$R^{48}$: H; or lower alkyl.

$R^{49}$: H; lower alkyl; —$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or $(CH_2)_sC_6H_4R^8$ (where $R^8$: H; F; Cl; $CF_3$; lower alkyl; lower alkenyl; or lower alkoxy).

$R^{50}$: H; methyl.

$R^{51}$: H; lower alkyl; lower alkenyl; —$(CH_2)_mOR^{55}$ (where $R^{55}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{52}$: H; lower alkyl; lower alkenyl; —$(CH_2)_mOR^{55}$ (where $R^{55}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{53}$: H; lower alkyl; lower alkenyl; —$(CH_2)_mOR^{55}$ (where $R^{55}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S (CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2 NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)C_6H_4R^8$ (where $R^8$: H; F; Cl; $CF_3$; lower alkyl; lower alkenyl; or lower alkoxy).

$R^{54}$: lower alkyl; lower alkenyl; or aryl-lower alkyl.

Among the building blocks A70 to A104 the following are preferred: A74 with $R^{22}$ being H, A75, A76, A77 with $R^{22}$ being H, A78 and A79.

The building block —B—CO— within templates (a1) and (a2) designates an L-amino acid residue. Preferred values for B are: —$NR^{20}CH(R^{71})$— and enantiomers of groups A5 with $R^2$ being H, A8, A22, A25, A38 with $R^2$ being H, A42, A47, and A50. Most preferred are

| | |
|---|---|
| Ala | L-Alanine |
| Arg | L-Arginine |
| Asn | L-Asparagine |
| Cys | L-Cysteine |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Pro(5RPhe) | (2S,5R)-5-phenylpyrrrolidine-2-carbocyclic acid |
| Ser | L-Serine |
| Thr | L-Threonine |
| Trp | L-Tryptophan |
| Tyr | L-Tyrosine |
| Val | L-Valine |
| Cit | L-Citrulline |
| Orn | L-Ornithine |
| tBuA | L-t-Butylalanine |
| Sar | Sarcosine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | L-1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |

| | |
|---|---|
| AcLys | L-N-Acetyllysine |
| Dpr | L-2,3-Diaminopropionic acid |
| A₂Bu | L-2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| Pip | L-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methvaline |
| MeLeu | L-N-Methylleucine |

In addition, the most preferred values for B also include groups of type A8" of (L)-configuration:

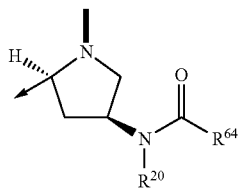

A8"

wherein $R^{20}$ is H or lower alkyl and $R^{64}$ is alkyl; alkenyl; —[(CH$_2$)$_u$—X]$_t$—CH$_3$ (where X is —O—; —NR$^{20}$—, or —S—; u=1-3, and t=1-6), aryl; aryl-lower alkyl; or heteroaryl-lower alkyl; especially those wherein $R^{64}$ is n-hexyl (A8"-21); n-heptyl (A8"-22); 4-(phenyl)benzyl (A8"-23); diphenylmethyl (A8"-24); 3-amino-propyl (A8"-25); 5-amino-pentyl (A8"-26); methyl (A8"-27); ethyl (A8"-28); isopropyl (A8"-29); isobutyl (A8"-30); n-propyl (A8"-31); cyclohexyl (A8"-32); cyclohexyl-methyl (A8"-33); n-butyl (A8"-34); phenyl (A8"-35); benzyl (A8"-36); (3-indolyl)methyl (A8"-37); 2-(3-indolyl)ethyl (A8"-38); (4-phenyl)phenyl (A8"-39); n-nonyl (A8"-40); CH$_3$—OCH$_2$CH$_2$—OCH$_2$— (A8"-41) and CH$_3$—(OCH$_2$CH$_2$)$_2$—OCH$_2$— (A8"-42).

The peptidic chain Z of the β-hairpin mimetics described herein is generally defined in terms of amino acid residues belonging to one of the following groups:

Group C —NR$^{20}$CH(R$^{72}$)CO—; "hydrophobic: small to medium-sized"

Group D —NR$^{20}$CH(R$^{73}$)CO—; "hydrophobic: large aromatic or heteroaromatic"

Group E —NR$^{20}$CH(R$^{74}$)CO—; "polar-cationic" and "urea-derived"

Group F —NR$^{20}$CH(R$^{84}$)CO—; "polar-non-charged or anionic"

Group H —NR$^{20}$—CH(CO—)—(CH$_2$)$_{4-7}$—CH(CO—)—NR$^{20}$—;
—NR$^{20}$—CH(CO—)—(CH$_2$)$_p$SS(CH$_2$)$_p$—CH(CO—)—NR$^{20}$—;
—NR$^{20}$—CH(CO—)—(—(CH$_2$)$_p$NR$^{20}$CO(CH$_2$)$_p$—CH(CO—)—NR$^{20}$—; and
—NR$^{20}$—CH(CO—)—(—(CH$_2$)$_p$NR$^{20}$CONR$^{20}$(CH$_2$)$_p$—CH(CO—)—NR$^{20}$—; "interstrand linkage"

Furthermore, the amino acid residues in chain Z can also be of formula -A-CO— or of formula —B—CO— wherein A and B are as defined above. Finally, Gly can also be an amino acid residue in chain Z, and Pro can be an amino acid residue in chain Z, too, with the exception of positions where interstrand linkages (H) are possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded heteroaromatic amino acids include tryptophan and histidine.

Group E comprises amino acids containing side chains with polar-cationic, acylamino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxyclic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, carboxylic acids and carboxylates, alkyl- or aryl phosphonates- and phosphates or tertiary amines. Genetically encoded polar-non-charged amino acids include asparagine, cysteine, glutamine, serine and threonine, but also aspartic acid and glutamic acid.

Group H comprises side chains of preferably (L)-amino acids at opposite positions of the β-strand region that can form an interstrand linkage. The most widely known linkage is the disulfide bridge formed by cysteines and homocysteines positioned at opposite positions of the β-strand. Various methods are known to form disulfide linkages including those described by: J. P. Tam et al. *Synthesis* 1979, 955-957; Stewart et al., *Solid Phase Peptide Synthesis*, 2d Ed., Pierce Chemical Company, Ill., 1984; Ahmed et al. *J. Biol. Chem.* 1975, 250, 8477-8482; and Pennington et al., *Peptides*, pages 164-166, Giralt and Andreu, Eds., ESCOM Leiden, The Netherlands, 1990. Most advantageously, for the scope of the present invention, disulfide linkages can be prepared using acetamidomethyl (Acm)-protective groups for cysteine. A well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

As mentioned earlier, positions for interstrand linkages are positions P4 and P 9 and/or P2 and P11 taken together. Such interstrand linkages are known to stabilize the β-hairpin conformations and thus constitute an important structural element for the design of β-hairpin mimetics.

Most preferred amino acid residues in chain Z are those derived from natural α-amino acids. Hereinafter follows a list of amino acids which, or the residues of which, are suitable for the purposes of the present invention, the abbreviations corresponding to generally adopted usual practice:

| three letter code | one letter code | |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |

-continued

| three letter code | | one letter code |
|---|---|---|
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| A$_2$Bu | 2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| Pro(4-OH)1 | (4S)-L-Hydroxyproline |
| Pro(4-OH)2 | (4R)-L-Hydroxyproline |
| Pip | L-Pipecolic acid |
| $^D$Pip | D-Pipecolic acid |
| OctG | L-Octylglycine |
| NGly | N-Methylglycine |
| MePhe | L-N-Methylphenylalanine |
| MeNle | L-N-Methylnorleucine |
| MeAla | L-N-Methylalanine |

-continued

| | |
|---|---|
| MeIle | L-N-Methylisoleucine |
| MeVal | L-N-Methylvaline |
| MeLeu | L-N-Methylleucine |
| DimK | L-(N',N'Dimethyl)-lysine |
| Lpzp | L-Piperazinic acid |
| Dpzp | D-Piperazinic acid |
| Isorn | L-(N',N'-diisobutyl)-ornithine |
| PipAla | L-2-(4'-piperidinyl)-alanine |
| PirrAla | L-2-(3'-pyrrolidinyl)-alanine |
| Ampc | 4-Amino-piperidine-4-carboxylic acid |
| NMeR | L-N-Methylarginine |
| NMeK | L-N-Methyllysine |
| NMePhe | L-N-Methylphenylalanine |
| IPegK | L-2-Amino-6-{2-[2-(2-methoxy-ethoxy)ethoxy]acetylamino}-hexanoic acid |
| SPegK | L-2-Amino-6-[2-(2methoxy-ethoxy)-acetylamino]-hexanoic acid |
| Dab | L-2,4-Diamino-butyric acid |
| IPegDab | L-2-Amino-4{2-[2-(2-methoxy-ethoxy)-ethoxy]-acetylamino}-butyric acid |
| SPegDab | L-2-Amino-4[2-(2-methoxy-ethoxy)-acetylamino] butyric acid |
| 4-PyrAla | L-2-(4'Pyridyl)-alanine |
| OrnPyr | L-2-Amino-5-[(2'carbonylpyrazine)]amino-pentanoic acid |
| BnG | N-Benzylglycine |
| AlloT | Allo-Threonin |
| Aoc | 2-(S)-Aminooctanoic acid |
| Cpa | L-Cyclo-Propylalanine |

Particularly preferred residues for group C are:

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert.-Butylglycine |
| Cha | L-Cyclohexylalanine |
| $C_4$al | L-3-Cyclobutylalanine |
| $C_5$al | L-3-Cyclopentylalanine |
| Nle | L-Norleucine |
| hCha | L-Homo-cyclohexylalanine |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| Aoc | 2-(S)-Aminooctanoic acid |
| Cpa | L-Cyclo-Propylalanine |

Particularly preferred residues for group D are:

| | |
|---|---|
| His | L-Histidine |
| Phe | L-Phenylalanine |
| Trp | L-Tryptophan |
| Tyr | L-Tyrosine |
| Phg | L-Phenylglycine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |
| PirrAla | L-2-(3'-pyrrolidinyl)-alanine |
| NMePhe | L-N-Methylphenylalanine |
| 4-PyrAla | L-2-(4'Pyridyl)-alanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A$_2$Bu | L-2,4-Diaminobutyric acid |
| Dbu | (S)-2,3-Diaminobutyric acid |
| Phe(pNH$_2$) | L-para-Aminophenylalanine |
| Phe(mNH$_2$) | L-meta-Aminophenylalanine |
| Phe(oNH$_2$) | L-ortho-Aminophenylalanine |
| hArg | L-Homo-arginine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| DimK | L-(N',N'Dimethyl)-lysine |
| Isorn | L-(N',N'-diisobutyl)-ornithine |
| NMeR | L-N-Methylarginine |
| NMeK | L-N-Methyllysine |
| IPegK | L-2-Amino-6-{2-[2-(2-methoxy-ethoxy)ethoxy]acetylamino}-hexanoic acid |
| SPegK | L-2-Amino-6-[2-(2methoxy-ethoxy)-acetylamino]-hexanoic acid |
| Dab | L-2,4-Diamino-butyric acid |
| IPegDab | L-2-Amino-4{2-[2-(2-methoxy-ethoxy)-ethoxy]-acetylamino}-butyric acid |
| SPegDab | L-2-Amino-4[2-(2-methoxy-ethoxy)-acetylamino] butyric acid |
| OrnPyr | L-2-Amino-5-[(2'carbonylpyrazine)]aminopentanoic |
| PipAla | L-2-(4'-piperidinyl)-alanine |

Particularly preferred residues for group F are

| | |
|---|---|
| Asn | L-Asparagine |
| Asp | L-Aspartic acid |
| Cys | L-Cysteine |
| Gln | L-Glutamine |
| Glu | L-Glutamic acid |
| Ser | L-Serine |
| Thr | L-Threonine |
| AlloThr | Allo Threonine |
| Cit | L-Citrulline |
| Pen | L-Penicillamine |
| AcLys | L-N$^\epsilon$-Acetyllysine |
| hCys | L-Homo-cysteine |
| hSer | L-Homo-serine |

Generally, the peptidic chain Z within the β-hairpin mimetics of the invention comprises 12 amino acid residues. The positions P1 to P12 of each amino acid residue in the chain Z are unequivocally defined as follows: P1 represents the first amino acid in the chain Z that is coupled with its N-terminus to the C-terminus of the templates (b)-(p), or of group —B—CO— in template (a1), or of group -A-CO— in template (a2); and P12 represents the last amino acid in the chain Z that is coupled with its C-terminus to the N-terminus of the templates (b)-(p), or of group -A-CO— in template (a1), or of group —B—CO— in template (a2). Each of the positions P1 to P12 will preferably contain an amino acid residue belonging to one of the above types C, D, E, F, H, or of formula -A-CO— or of formula —B—CO—, or being Gly, or Pro as follows:

The α-amino acid residues in positions 1 to 12 of the chain Z are preferably:
P1: of type C or of type D or of type E or of type F;
P2: of type D;
P3: of type C, or the residue is Gly or Pro;
P4: of type C or of type E or of type F, or the residue is Gly or Pro;
P5: of type E, or the residue is Gly or Pro;
P6: of type E, of type C or of type F or of formula -A-CO—, or the residue is Gly or Pro;
P7: of type C or of type E or of type F or of formula —B—CO—;
P8: of type D, or of type F;
P9: of type E or of type F or of type C;
P10: of type E;
P11: of type F or of type C, or the residue is Gly or Pro; and
P12: of type C or of type D or of type E, or of type F; or
P4 and P9 and/or P2 and P11, taken together, can form a group of type H; and
at P6, P10 and P11 also D-isomers being possible;
or, alternatively, within the less preferred embodiment mentioned earlier herein above:
P1: of type C or of type D or of type E, or of type F;
P2: of type F or of type C, or the residue is Gly or Pro;
P3: of type E;
P4: of type E or of type F or of type C;
P5: of type D, or of Type F;
P6: of type C or of type E or of type F or of formula —B—CO—;
P7: of type C or of type F or of formula -A-CO—, or the residue is Gly or Pro;
P8: of type E, or the residue is Gly or Pro;
P9: of type C or of type E or of type F, or the residue is Gly or Pro;
P10: of type C, or the residue is Gly or Pro;
P11: of type D; and
P12: of type C or of type D or of type E or of type F; or
P4 and P9 and/or P2 and P11, taken together, can form a group of type H; and
at P2, P3, and P7 also D-isomers being possible.

If n is 12, the α-amino acid residues in positions 1 to 12 are most preferably:
P1: Ala, Cit, Thr, Thr, Asp, Glu;
P2: Trp, Tyr;
P3: Ile, Val, Nle, Chg, Cha;
P4: Dab, Lys, Gln;
P5: Lys, Dab, Orn;
P6: Dab, $^D$Dab; Lys;
P7: H is, Lys, Gln, Dab;
P8: Tyr, Trp, Ser;
P9 Dab, Lys;
P10: Dab, Lys;
P11: Ala, Abu, Thr, Gly, Pro, Hse, Ile, Nva, $^D$Ala, $^D$Val, Aib, Nle, Chg, Cha, Gln, Asp, Glu, Cpa, t-BuG, Leu, Val, Asn;
P12: Dab, Lys, Gin, Ser;
at P6, P10 and P11 are D-Isomers being possible.

Particularly preferred (β-hairpin peptidomimetics of the invention include those described in Examples 1, 2, 6, 16, 19, 22, 24, 25, 28, 29, 32, 35, 40, 41, 49, 50.

The processes of the invention can advantageously be carried out as parallel array syntheses to yield libraries of template-fixed β-hairpin peptidomimetics of the above general formula I. Such parallel syntheses allow one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (Rink H, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl)Fmoc-aminomethyl)phenoxyacetamido) aminomethyl] PS resin, 4-[(((2,4-dimethoxyphenyl)Fmoc-aminomethyl)phenoxyacetamido)aminomethyl]-4-methylbenzydrylamine PS resin (Rink amide MBHA PS Resin), and 4-[(((2,4-dimethoxyphenyl)Fmoc-aminomethyl) phenoxyacetamido)aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the above formula I.

A number of reaction vessels (normally 24 to 192, typically 96), equal to the total number of compounds to be synthesized by the parallel method, are loaded with 25 to 1000 mg, preferably 100 mg, of the appropriate functionalized solid support, preferably 1 to 3% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2, 4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Florsheimer & Riniker, *Peptides* 1991, 1990 131) which is also cleaved with 1% TFA/DCM in order to yield a peptide fragment containing all acid labile side-chain protective groups; and, in particular, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)

| | |
|---|---|
| Cbz | benzyloxycarbonyl |
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e.g. also in the side-chain of aspartic and glutamic acid) by conversion into esters with the alcohol components

| | |
|---|---|
| tBu | tert.-butyl |
| Bn | benzyl |
| Me | methyl |
| Ph | phenyl |
| Pac | Phenacyl |
| | Allyl |
| Tse | trimethylsilylethyl |
| Tce | trichloroethyl; | for the guanidino group (as is present e.g. in the side-chain of arginine)

| | |
|---|---|
| Pmc | 2,2,5,7,8-pentamethylchroman-6-sulfonyl |
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e.g. in the side-chain of threonine and serine)

| | |
|---|---|
| tBu | tert.-butyl |
| Bn | benzyl |
| Trt | trityl | and for the mercapto group (as is present e.g. in the side-chain of cysteine)

| | |
|---|---|
| Acm | acetamidomethyl |
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; *Synthesis,* 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-)1,3,3-tetramethyluronium terafluoroborate (TBTU), or hexafluorophosphate (HBTU, Knorr et al., *Tetrahedron Lett.* 1989, 30, 1927-1930), or 1-benzotriazol-1-[bis(dimethylamino)methylene]-5-chloro-hexafluorophosphate-1,3-oxide (HCTU); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N', N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;
2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent and by-product removal by methods such as TLC, GC, or inspection of the washings.

The above described procedure of reacting the resin-bound compound with reagents within the reaction wells followed by removal of excess reagents, by-products and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2CH_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced. For the formation of pegylated amino acids such as IPegK, or SPegK, preferably a solution of 5 equivalents of HATU (N—[(dimethylamino)-1H-1,2,3-triazolo[4,5-b]pyridin-1-ylmethylene]-N-methyl-methanaminium hexafluorophosphate N-oxide) in dry DMF and a solution of 10 equivalents of DIPEA (Diisopropyl ethaylamine) in dry DMF and 5 equivalents of 2-[2-(2-methoxyethoxy)ethoxy]acetic acid (lPeg) and, respectively, 2-(2-methoxyethoxy)acetic acid (sPeg), is applied to the liberated amino group of the appropriate amino acid side chain for 3 h. The procedure is thereafter repeated for another 3 h with a fresh solution of reagents after filtering and washing the resin.

Before this fully protected linear peptide is detached from the solid support, it is also possible, if desired, to form (an) interstrand linkage(s) between side-chains of appropriate amino acid residues at opposite positions of the β-strand region.

Interstrand linkages and their formation have been discussed above, in connection with the explanations made regarding groups of the type H which can, for example, be disulfide bridges formed by cysteine and homocysteine residues at opposite positions of the β-strand; or lactam bridges formed by glutamic and aspartic acid residues linking ornithine and, respectively, lysine residues, or by glutamic acid residues linking 2,4-diaminobutyric acid residues located at opposite β-strand positions by amide bond formation. The formation of such interstrand linkages can be effected by methods well known in the art.

For the formation of disulfide bridges preferably a solution of 10 equivalents of iodine solution is applied in DMF or in a mixture of $CH_2CH_2$/MeOH for 1.5 h which is repeated for another 3 h with a fresh iodine solution after filtering of the iodine solution, or in a mixture of DMSO and acetic acid solution, buffered with 5% with $NaHCO_3$ to pH 5-6 for 4 h, or in water after having been adjusted to pH 8 with ammonium hydroxide solution by stirring for 24 h or ammonium acetate buffer adjusted to pH 8 in the presence of air, or in a solution of NMP and tri-n-butylphosphine (preferably 50 eq.).

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected cyclic peptide derivative of formula I is obtained as end-product. Depending on its purity, this peptide derivative can be used directly for biological assays, or it has to be further purified, for example by preparative HPLC.

Alternatively the detachment, cyclisation and complete deprotection of the fully protected peptide from the solid support can be achieved manually in glass vessels.

As mentioned earlier, it is thereafter possible, if desired, to convert a fully deprotected product of formula I thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The template starting materials of formula II used in the processes of the invention, pre-starting materials therefor, and the preparation of these starting and pre-starting materials are described in International Application PCT/EP02/01711, published as WO 02/070547 A1.

The β-hairpin peptidomimetics of the invention can be used in a wide range of applications in order to inhibit the growth of or to kill microorganisms. In particular they can be used to selectively inhibit the growth of or to kill microorganisms such as *Pseudomonas aeruginosa*.

They can be used for example as disinfectants or as preservatives for materials such as foodstuffs, cosmetics, medicaments and other nutrient-containing materials. The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomimetics or in combination with other antimicrobial agents. The β-hairpin peptidomimetics may be administered per se or may be applied as an appropriate formulation together with carriers, diluents or excipients well known in the art.

When used to treat or prevent infections or diseases related to such infections, particularly infections related to respiratory diseases such as cystic fibrosis, emphysema and asthma; infections related to skin or soft tissue diseases such as surgical wounds, traumatic wounds and burn wounds; infections related to gastrointestinal diseases such as epidemic diarrhea, necrotizing enterocolitis and typhlitis; infections related to eye diseases such as keratitis and endophthalmitis; infections related to ear diseases such as otitis, infections related to CNS diseases such as brain abscess and meningitis; infections related to bone diseases such as osteochondritis and osteomyelitis; infections related to cardiovascular diseases such as endocartitis and pericarditis; or infections related to gastrourinal diseases such as epididymitis, prostatitis and urethritis; the β-hairpin peptidomimetics can be administered singly, as mixtures of several β-hairpin peptidomimetics, in combination with other antimicrobial or antibiotic agents, or anti cancer agents, or antiviral (e.g. anti-HIV) agents, or in combination with other pharmaceutically active agents. The β-hairpin peptidomimetics can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, disintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free base forms.

The β-hairpin peptidomimetics of the invention, or compositions thereof, will generally be used in an amount effective to achieve the intended purpose. It is to be understood that the amount used will depend on a particular application.

For example, for use as a desinfectant or preservative, an antimicrobially effective amount of a β-hairpin peptidomimetic of the invention, or a composition thereof, is applied or added to the material to be desinfected or preserved. By antimicrobially effective amount is meant an amount of a fβ-hairpin peptidomimetic of the invention, or a composition thereof, that inhibits the growth of, or is lethal to, a target microbe population. While the antimicrobially effective amount will depend on a particular application, for use as desinfectants or preservatives the β-hairpin peptidomimetics of the invention, or compositions thereof, are usually added or applied to the material to be desinfected or preserved in relatively low amounts. Typically, the β-hairpin peptidomimetics of the invention comprise less than about 5% by weight of a desinfectant solution or material to be preserved, preferably less than 1% by weight and more preferably less than 0.1% by weight. An ordinary skilled expert will be able to determine antimicrobially effective amounts of particular (β-hairpin pepdidomimetics of the invention for particular applications without undue experimentation using, for example, the in vitro assays provided in the examples.

For use to treat or prevent microbial infections or diseases related to such infections, the β-hairpin pepidomimetics of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art, especially in view of the detailed disclosure provided herein.

As in the case of desinfectants and preservatives, for topical administration to treat or prevent bacterial infections a therapeutically effective dose can be determined using, for example, the in vitro assays provided in the examples. The treatment may be applied while the infection is visible, or even when it is not visible. An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture), the MIC, as determined in cell culture (i.e. the concentration of a test compound that is lethal to 100% of a cell culture). Such information can be used to more accurately determine useful doses in humans.

Initial dosages can also be determined from in vivo data, e.g. animal models, using techniques that are well known in the art. One having ordinary skills in the art could readily optimize administration to humans based on animal data.

Dosage amount for applications as antimicrobial agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The antimicrobial therapy may be repeated intermittently while infections are detectable or even when they are not detectable. The therapy may be provided alone or in combination with other drugs, such as for example antibiotics or other antimicrobial agents.

Normally, a therapeutically effective dose of the β-hairpin peptidomimetics described herein will provide therapeutic benefit without causing substantial toxicity.

Hemolysis of red blood cells is often employed for assessment of toxicity of related compounds such as protegrin or tachyplesin. Values are given as %-lysis of red blood cells observed at a concentration of 100 µg/ml. Typical values determined for cationic peptides such as protegrin and tachyplesin range between 30-40% with average MIC-values of 1-5 □µg/ml over a wide range of pathogens. Normally, β-hairpin peptidomimetics of the invention will show hemolysis in a range of 0.5-10%, often in a range of 1-5%, at activity levels comparable to those mentioned above for protegrin and tachyplesin. Thus preferred compounds exhibit low MIC-values and low %-hemolysis of red blood cells observed at a concentration of 100 µg/ml.

Toxicity of the β-hairpin peptidomimetics of the invention herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the invention in more detail but are not intended to limit its scope in any way. The following abbreviations are used in these Examples:
HBTU: 1-benzotriazol-1-yl-tetramethylurounium hexafluorophosphate (Knorr et al. *Tetrahedron Lett.* 1989, 30, 1927-1930);
HCTU: 1-Benzotriazol 1-[bis(dimethylamino)methylene]-5-chloro-hexafluorophosphate-1,3-oxide
HOBt: 1-hydroxybenzotriazole;
DIEA: diisopropylethylamine;
HOAT: 7-aza-1-hydroxybenzotriazole;
HATU: O-(7-aza-benzotriazole-1-yl)-N,N,N',N'-tetramethyluronoium hexafluorophosphate (Carpino et al. *Tetrahedron Lett.* 1994, 35, 2279-2281).

EXAMPLES

1. Peptide Synthesis

Coupling of the First Protected Amino Acid Residue to the Resin 0.5 g of 2-chlorotritylchloride resin (Barlos et al. *Tetrahedron Lett.* 1989, 30, 3943-3946) (0.83 mMol/g, 0.415 mmol) was filled into a dried flask. The resin was suspended in $CH_2CH_2$ (2.5 ml) and allowed to swell at room temperature under constant stirring for 30 min. The resin was treated with 0.415 mMol (1 eq) of the first suitably protected amino acid residue (see below) and 284 µl (4 eq) of diisopropyl-ethylamine (DIEA) in $CH_2CH_2$ (2.5 ml), the mixture was shaken at 25° C. for 4 hours. The resin was shaken ($CH_2CH_2$/MeOH/DIEA:17/2/1), 30 ml for 30 min; then washed in the following order with $CH_2CH_2$ (1×), DMF (1×), $CH_2CH_2$ (1×), MeOH (1×), $CH_2CH_2$ (1×), MeOH (1×), $CH_2CH_2$ (2×), $Et_2O$ (2×) and dried under vacuum for 6 hours.

Loading was typically 0.6-0.7 mMol/g.

The following preloaded resin was prepared: Fmoc-Pro-2-chlorotritylresin.

Synthesis of the Fully Protected Peptide Fragment

The synthesis was carried out using a Syro-peptide synthesizer (Multisyntech) using 24 to 96 reaction vessels. In each vessel were placed 60 mg (weight of the resin before loading) of the above resin. The following reaction cycles were programmed and carried out:

| Step | Reagent | Time |
|---|---|---|
| 1 | $CH_2Cl_2$, wash and swell (manual) | 3 × 1 min. |
| 2 | DMF, wash and swell | 1 × 5 min |
| 3 | 40% piperidine/DMF | 2 × 5 min. |
| 4 | DMF, wash | 5 × 2 min. |
| 5 | 5 equiv. Fmoc amino acid/DMF +5 eq. HCTU +5 eq. DIEA | 2 × 60 min. |
| 6 | DMF, wash | 4 × 2 min. |
| 7 | $CH_2Cl_2$, wash (at the end of the synthesis) | 3 × 2 min. |

Steps 3 to 6 are repeated to add each amino-acid.

After the synthesis of the fully protected peptide fragment had been terminated, then subsequently the cleavage, cyclization and work up procedure as described hereinbelow, was used for the preparation of the peptides.

Analytical Methods:

Method 1:

Analytical HPLC retention times (RT, in minutes) were determined using an Jupiter Proteo column (90 A, 150×2.0 mm, cod. 00F4396-B0-Phenomenex) with the following solvents A ($H_2O$+0.1% TFA) and B ($CH_3CN$+0.1% TFA) and the gradient: 0 min: 95% A, 5% B; 20 min: 40% A 60% B; 21-23 min: 0% A, 100% B; 23.1-30 min: 95% A, 5% B.

Method 2:

Analytical HPLC retention times (RT, in minutes) were determined using an Aquity UPLC BEH C18 column (1.7 µm, 100×2.1 mm, cod. 186002352-Waters) with the following solvents A ($H_2O$+0.1% TFA) and B ($CH_3CN$+0.085% TFA) and the gradient: 0 min: 95% A, 5% B; 0.2 min: 95% A 5% B; 4 min: 35% A, 65% B; 4.2 min: 5% A, 95% B; 4.25 min: 95% A, 5% B; 4.9 min: 95% A, 5% B.

Procedure: Cleavage, Cyclization and Work Up of Backbone Cyclized Peptides

Cleavage, Backbone Cyclization and Purification of the Peptide

After assembly of linear peptides, the resin was suspended in 1 ml (0.39 mMol) of 1% TFA in $CH_2CH_2$ (v/v) for 3 minutes and filtered, and the filtrate was neutralized with 1 ml (1.17 mMol, 3 eq.) of 20% DIEA in $CH_2CH_2$ (v/v). This procedure was repeated twice to ensure completion of the cleavage. The resin was washed with 2 ml of $CH_2CH_2$. The $CH_2CH_2$ layer was evaporated to dryness.

The fully protected linear peptide was solubilised in 8 ml of dry DMF. Then 2 eq. of HATU in dry DMF (1 ml) and 4 eq. of DIPEA in dry DMF (1 ml) were added to the peptide, followed by stirring for 16 h. The volatiles were evaporated to dryness. The crude cyclic peptide was dissolved in 7 ml of $CH_2CH_2$ and extracted with 10% acetonitrile in water (4.5 ml) three times. The $CH_2CH_2$ layer was evaporated to dryness. To fully deprotect the peptide, 3 ml of cleavage cocktail TFA:TIS:$H_2O$ (95:2.5:2.5) were added, and the mixture was stirred for 2.5 h. The volatile was evaporated to dryness and the crude peptide was dissolved in 20% AcOH in water (7 ml) and extracted with diisopropyl ether (4 ml)

for three times. The aqueous layer was collected and evaporated to dryness, and the residue was purified by preparative reverse phase LC-MS.

After lyophilisation the products were obtained as white powders and analysed by HPLC-ESI-MS analytical methods as described above. The analytical data comprising purity after preparative HPLC and ESI-MS are shown in Table 1.

Examples 1-50, are shown in Table 1. The peptides were synthesized starting with the amino acid L-Pro which was grafted to the resin. Starting resin was Fmoc-Pro-2-chlorotrityl resin, which was prepared as described above. The linear peptides were synthesized on solid support according to the procedure described above in the following sequence: Resin-Pro-$^D$Pro-P12-P11-P10-P9-P8-P7-P6-P5-P4-P3-P2-P1. Ex. 1-50, were cleaved from the resin, cyclized, deprotected and purified as indicated by preparative reverse phase LC-MS.

After lyophilisation the products were obtained as white powders and analysed by HPLC-ESI-MS methods as described above.

HPLC-retention times (minutes) were determined using the analytical methods as described above. Examples 1 to 39 were analysed with method 1, for Examples 40-50 method 2 was used:

Ex. 1 (8.87), Ex. 2 (9.26), Ex. 3 (9.34), Ex. 4 (9.45), Ex. 5 (9.48), Ex. 6 (9.44), Ex. 7 (10.11), Ex. 8 (9.99), Ex. 9 (10.22), Ex. 10 (9.76), Ex. 11 (10.56), Ex. 12 (11.37), Ex. 13 (9.13), Ex. 14 (9.34), Ex. 15 (8.80), Ex. 16 (9.23); Ex. 17 (9.65), Ex. 18 (9.18), Ex. 19 (8.37), Ex. 20 (8.86), Ex. 21 (8.78), Ex. 22 (9.32), Ex. 23 (9.58), Ex. 24 (9.27), Ex. 25 (9.31), Ex. 26 (9.24), Ex. 27 (9.23), Ex. 28 (9.34), Ex. 29 (9.66), Ex. 30 (9.88), Ex. 31 (9.62), Ex. 32 (8.86), Ex. 33 (9.73), Ex. 34 (10.46), Ex. 35 (9.21), Ex. 36 (9.80), Ex. 37 (9.73), Ex. 38 (9.20), Ex. 39 (9.53), Ex. 40 (2.07), Ex. 41 (1.77), Ex. 42 (1.66), Ex. 43 (1.67), Ex. 44 (1.81), Ex. 45 (1.87), Ex. 46 (1.81), Ex. 47 (1.83), Ex. 48 (1.79), Ex. 49 (1.88), Ex. 50 (2.17).

TABLE 1

Examples

| Example | Sequ. ID | P1 | P2 | P3 | P4 | P5 | P6 | P7 | P8 | P9 | P10 | P11 | P12 | Template | Purity %[a] | [M + 2H]/2 |
|---|---|---|---|---|---|---|---|---|---|---|---|---|---|---|---|---|
| 1 | SEQ ID NO: 1 | Thr | Trp | Ile | Dab | Lys | Dab | Dab | Trp | Dab | Dab | Ala | Dab | $^D$Pro$^L$Pro | 95 | 790.9 |
| 2 | SEQ ID NO: 2 | Thr | Trp | Ile | Dab | Lys | Dab | Dab | Trp | Dab | Dab | Gly | Dab | $^D$Pro$^L$Pro | 95 | 783.9 |
| 3 | SEQ ID NO 3 | Thr | Trp | Ile | Dab | Lys | Dab | Dab | Trp | Dab | Dab | $^D$Ala | Dab | $^D$Pro$^L$Pro | 95 | 791.1 |
| 4 | SEQ ID NO 4 | Thr | Trp | Ile | Dab | Lys | Dab | Dab | Trp | Dab | Dab | $^D$Val | Dab | $^D$Pro$^L$Pro | 95 | 805.2 |
| 5 | SEQ ID NO: 5 | Thr | Trp | Ile | Dab | Lys | Dab | Dab | Trp | Dab | Dab | Aib | Dab | $^D$Pro$^L$Pro | 86 | 798.0 |
| 6 | SEQ ID NO: 6 | Thr | Trp | Ile | Dab | Lys | Dab | Dab | Trp | Dab | Dab | Abu | Dab | $^D$Pro$^L$Pro | 86 | 797.9 |
| 7 | SEQ ID NO: 7 | Thr | Trp | Ile | Dab | Lys | Dab | Dab | Trp | Dab | Dab | Leu | Dab | $^D$Pro$^L$Pro | 95 | 812.5 |
| 8 | SEQ ID NO: 8 | Thr | Trp | Ile | Dab | Lys | Dab | Dab | Trp | Dab | Dab | Ile | Dab | $^D$Pro$^L$Pro | 89 | 812.6 |
| 9 | SEQ ID NO: 9 | Thr | Trp | Ile | Dab | Lys | Dab | Dab | Trp | Dab | Dab | Nle | Dab | $^D$Pro$^L$Pro | 39 | 812.3 |
| 10 | SEQ ID NO: 10 | Thr | Trp | Ile | Dab | Lys | Dab | Dab | Trp | Dab | Dab | Nva | Dab | $^D$Pro$^L$Pro | 87 | 805.1 |
| 11 | SEQ ID NO: 11 | Thr | Trp | Ile | Dab | Lys | Dab | Dab | Trp | Dab | Dab | Chg | Dab | $^D$Pro$^L$Pro | 82 | 825.7 |
| 12 | SEQ ID NO: 12 | Thr | Trp | Ile | Dab | Lys | Dab | Dab | Trp | Dab | Dab | Cha | Dab | $^D$Pro$^L$Pro | 95 | 831.9 |
| 13 | SEQ ID NO: 13 | Thr | Trp | Ile | Dab | Lys | Dab | Dab | Trp | Dab | Dab | Gln | Dab | $^D$Pro$^L$Pro | 87 | 819.6 |
| 14 | SEQ ID NO: 14 | Thr | Trp | Ile | Dab | Lys | Dab | Dab | Trp | Dab | Dab | Asp | Dab | $^D$Pro$^L$Pro | 80 | 813.5 |
| 15 | SEQ ID NO: 15 | Thr | Trp | Ile | Dab | Lys | Dab | Dab | Trp | Dab | Dab | Glu | Dab | $^D$Pro$^L$Pro | 83 | 820.1 |
| 16 | SEQ ID NO: 16 | Thr | Trp | Ile | Dab | Lys | Dab | Dab | Trp | Dab | Dab | Thr | Dab | $^D$Pro$^L$Pro | 95 | 806.1 |
| 17 | SEQ ID NO: 17 | Thr | Trp | Ile | Dab | Lys | Dab | Dab | Trp | Dab | Dab | Pro | Dab | $^D$Pro$^L$Pro | 85 | 804.0 |
| 18 | SEQ ID NO: 18 | Cit | Trp | Ile | Dab | Lys | Dab | Dab | Trp | Dab | Dab | Ala | Dab | $^D$Pro$^L$Pro | 95 | 819.6 |
| 19 | SEQ ID NO: 19 | Thr | Tyr | Ile | Dab | Lys | Dab | Dab | Trp | Dab | Dab | Ala | Dab | $^D$Pro$^L$Pro | 95 | 779.9 |
| 20 | SEQ ID NO: 20 | Thr | Trp | Ile | Dab | Lys | Dab | Dab | Tyr | Dab | Dab | Ala | Dab | $^D$Pro$^L$Pro | 95 | 779.5 |
| 21 | SEQ ID NO: 21 | Thr | Trp | Ile | Dab | Lys | Dab | His | Trp | Dab | Dab | Ala | Dab | $^D$Pro$^L$Pro | 95 | 810.0 |
| 22 | SEQ ID NO: 22 | Ala | Trp | Ile | Dab | Lys | Dab | Dab | Trp | Dab | Dab | Ala | Dab | $^D$Pro$^L$Pro | 95 | 776.2 |
| 23 | SEQ ID NO: 23 | Ala | Trp | Ile | Dab | Dab | Dab | Dab | Trp | Dab | Dab | Val | Dab | $^D$Pro$^L$Pro | 95 | 776.4 |
| 24 | SEQ ID NO: 24 | Thr | Trp | Ile | Lys | Lys | Dab | Dab | Trp | Dab | Dab | Ala | Dab | $^D$Pro$^L$Pro | 87 | 805.1 |
| 25 | SEQ ID NO: 25 | Thr | Trp | Ile | Dab | Lys | Lys | Dab | Trp | Dab | Dab | Ala | Dab | $^D$Pro$^L$Pro | 95 | 805.0 |
| 26 | SEQ ID NO: 26 | Thr | Trp | Ile | Dab | Lys | Dab | Lys | Trp | Dab | Dab | Ala | Dab | $^D$Pro$^L$Pro | 87 | 805.2 |
| 27 | SEQ ID NO: 27 | Thr | Trp | Ile | Dab | Lys | Dab | Dab | Trp | Lys | Dab | Ala | Dab | $^D$Pro$^L$Pro | 95 | 805.1 |
| 28 | SEQ ID NO: 28 | Thr | Trp | Ile | Dab | Lys | Dab | Dab | Trp | Dab | Dab | Ala | Lys | $^D$Pro$^L$Pro | 95 | 805.0 |
| 29 | SEQ ID NO: 29 | Thr | Trp | Ile | Gln | Lys | Dab | Dab | Trp | Dab | Dab | Ala | Dab | $^D$Pro$^L$Pro | 86 | 805.2 |
| 30 | SEQ ID NO: 30 | Thr | Trp | Ile | Gln | Lys | Dab | Dab | Trp | Dab | Dab | Val | Dab | $^D$Pro$^L$Pro | 88 | 819.1 |
| 31 | SEQ ID NO: 31 | Thr | Trp | Nle | Dab | Lys | Dab | Dab | Trp | Dab | Dab | Ala | Dab | $^D$Pro$^L$Pro | 95 | 791.1 |
| 32 | SEQ ID NO: 32 | Thr | Trp | Val | Dab | Lys | Dab | Dab | Trp | Dab | Dab | Ala | Dab | $^D$Pro$^L$Pro | 95 | 784.0 |
| 33 | SEQ ID NO: 33 | Thr | Trp | Chg | Dab | Lys | Dab | Dab | Trp | Dab | Dab | Ala | Dab | $^D$Pro$^L$Pro | 95 | 804.4 |
| 34 | SEQ ID NO: 34 | Thr | Trp | Cha | Dab | Lys | Dab | Dab | Trp | Dab | Dab | Ala | Dab | $^D$Pro$^L$Pro | 95 | 811.5 |
| 35 | SEQ ID NO: 35 | Thr | Trp | Ile | Dab | Lys | Dab | Dab | Trp | Dab | Dab | Hse | Dab | $^D$Pro$^L$Pro | 95 | 806.4 |
| 36 | SEQ ID NO: 36 | Thr | Trp | Ile | Dab | Lys | Dab | Dab | Trp | Dab | Dab | t-BuG | Dab | $^D$Pro$^L$Pro | 95 | 812.5 |
| 37 | SEQ ID NO: 37 | Thr | Trp | Ile | Dab | Lys | Dab | Dab | Trp | Dab | Dab | Cpa | Dab | $^D$Pro$^L$Pro | 89 | 811.3 |
| 38 | SEQ ID NO: 38 | Thr | Trp | Ile | Dab | Lys | Dab | Dab | Trp | Dab | Dab | Asn | Dab | $^D$Pro$^L$Pro | 95 | 813.1 |
| 39 | SEQ ID NO: 39 | Thr | Trp | Ile | Dab | Lys | Dab | Gln | Trp | Dab | Dab | Ala | Dab | $^D$Pro$^L$Pro | 95 | 805.2 |
| 40 | SEQ ID NO: 40 | Thr | Trp | Ile | Gln | Lys | Dab | Dab | Trp | Dab | Dab | Ala | Gln | $^D$Pro$^L$Pro | 95 | 819.6 |
| 41 | SEQ ID NO: 41 | Thr | Trp | Ile | Dab | Lys | $^D$Dab | Dab | Trp | Dab | Dab | Ala | Dab | $^D$Pro$^L$Pro | 91 | 791.2 |
| 42 | SEQ ID NO: 42 | Asp | Tyr | Ile | Dab | Lys | $^D$Dab | Dab | Trp | Dab | Dab | Ala | Dab | $^D$Pro$^L$Pro | 85 | 786.6 |
| 43 | SEQ ID NO: 43 | Asp | Tyr | Ile | Dab | Orn | $^D$Dab | Dab | Trp | Dab | Dab | Ala | Dab | $^D$Pro$^L$Pro | 85 | 779.6 |
| 44 | SEQ ID NO: 44 | Glu | Trp | Ile | Dab | Lys | $^D$Dab | Dab | Trp | Dab | Dab | Ala | Dab | $^D$Pro$^L$Pro | 78 | 805.1 |
| 45 | SEQ ID NO: 45 | Glu | Trp | Ile | Dab | Lys | $^D$Dab | Dab | Trp | Dab | Dab | Ala | Gln | $^D$Pro$^L$Pro | 82 | 819.2 |
| 46 | SEQ ID NO: 46 | Glu | Trp | Ile | Dab | Lys | $^D$Dab | Dab | Trp | Dab | Dab | Ala | Dap | $^D$Pro$^L$Pro | 83 | 798.0 |
| 47 | SEQ ID NO: 47 | Glu | Trp | Ile | Dab | Orn | $^D$Dab | Dab | Trp | Dab | Dab | Ala | Dab | $^D$Pro$^L$Pro | 85 | 798.3 |
| 48 | SEQ ID NO: 48 | Thr | Trp | Ile | Dab | Orn | $^D$Dab | Dab | Trp | Dab | Dab | Ala | Dab | $^D$Pro$^L$Pro | 86 | 784.1 |

TABLE 1-continued

Examples

| Example | Sequ. ID | P1 | P2 | P3 | P4 | P5 | P6 | P7 | P8 | P9 | P10 | P11 | P12 | Template | Purity %[a] | [M + 2H]/2 |
|---|---|---|---|---|---|---|---|---|---|---|---|---|---|---|---|---|
| 49 | SEQ ID NO: 49 | Thr | Trp | Ile | Dab | Orn | $^D$Dab | Dab | Trp | Dab | Dab | Ala | Ser | $^D$Pro$^L$Pro | 91 | 777.7 |
| 50 | SEQ ID NO: 50 | Glu | Trp | Ile | Gln | Lys | Dab | Dab | Ser | Dab | Dab | Ala | Ser | $^D$Pro$^L$Pro | 95 | 805.8 |

[a] %-puritity of compounds after prep. HPLC.

2. Biological Methods 2.1. Preparation of the Peptide Samples.

Lyophilized peptides were weighed on a Microbalance (Mettler MT5) and dissolved in sterile water to a final concentration of 1 mg/ml unless stated otherwise. Stock solutions were kept at +4° C., light protected.

2.2. Antimicrobial Activity of the Peptides.

The selective antimicrobial activities of the peptides were determined in 96-well plates (Nunclon polystyrene) by the standard NCCLS broth microdilution method (see ref 1, below) with slight modifications. Innocula of the microorganisms were diluted into Mueller-Hinton (MH) broth+ 0.02% BSA and compared with a 0.5 Mcfarland standard to give appr. $10^6$ colony forming units (CFU)/ml. Aliquots (50 µl) of inoculate were added to 50 µl of MH broth+0.02% BSA containing the peptide in serial two-fold dilutions. The following microorganisms were used to determine antibiotic selectivity of the peptides: *Escherichia coli* (ATCC 25922), *Pseudomonas aeruginosa* (*P. aeruginosa* ATCC 27853, P8191900, P1021903, P1021913, IMP 1 Livermore 3140). Antimicrobial activities of the peptides were expressed as the minimal inhibitory concentration (MIC) in µg/ml at which no visible growth was observed after 18-20 hours of incubation at 37° C.

2.3. Cytotoxicity Assay

The cytotoxicity of the peptides to HELA cells (Acc57) and COS-7 cells (CRL-1651) was determined using the MTT reduction assay [see ref. 2 and 3, below]. Briefly the method was as follows: HELA cells and COS-7 cells were seeded at $7.0 \times 10^3$ and, respectively, $4.5 \times 10^3$ cells per well and grown in 96-well microtiter plates for 24 hours at 37° C. at 5% $CO_2$. At this point, time zero (Tz) was determined by MTT reduction (see below). The supernatant of the remaining wells was discarded, and fresh medium and the peptides in serial dilutions of 12.5, 25 and 50 µM were dispensed into the wells. Each peptide concentration was assayed in triplicate. Incubation of the cells was continued for 48 hours at 37° C. at 5% $CO_2$. Wells were then washed once with phosphate buffered saline (PBS) and subsequently 100 µl MTT reagent (0.5 mg/ml in medium RPMI1640 and, respectively, DMEM) were added to the wells. This was incubated at 37° C. for 2 hours and subsequently the medium was aspirated and 100 µl isopropanol were added to each well. The absorbance at 595 nm of the solubilized product was measured ($OD_{595}$peptide). For each concentration averages were calculated from triplicates. The percentage of growth was calculated as follows: ($OD_{595}$peptide–$OD_{595}$Tz–$OD_{595}$Empty well)/($OD_{595}$Tz–$OD_{595}$Empty well)×100% and was plotted for each peptide concentration.

The LC 50 values (Lethal Concentration, defined as the concentration that kills 50% of the cells) were determined for each peptide by using the trend line function of EXCEL (Microsoft Office 2000) for the concentrations (50, 25, 12.5 and 0 µM), the corresponding growth percentages and the value –50, (=TREND (C50:C0,%50:%0,–50)). The GI 50 (Growth Inhibition) concentrations were calculated for each peptide by using a trend line function for the concentrations (50, 25, 12.5 and 0 µg/ml), the corresponding percentages and the value 50, (=TREND ($C_{50}$:$C_0$,%$_{50}$:%$_0$,50).

2.4. Hemolysis

The peptides were tested for their hemolytic activity against human red blood cells (hRBC). Fresh hRBC were washed three times with phosphate buffered saline (PBS) by centrifugation for 10 min at 2000×g. Peptides at a concentration of 100 µM were incubated with 20% v/v hRBC for 1 hour at 37° C. The final erythrocyte concentration was approximately $0.9 \times 10^9$ cells per ml. A value of 0% and, respectively, 100% cell lysis was determined by incubation of the hRBC in the presence of PBS alone and, respectively, 0.1% Triton X-100 in $H_2O$. The samples were centrifuged, the supernatant was 20-fold diluted in PBS buffer and the optical density (OD) of the sample at 540 nM was measured. The 100% lysis value ($OD_{540}H_2O$) gave an $OD_{540}$ of approximately 1.3-1.8. Percent hemolysis was calculated as follows: ($OD_{540}$peptide/$OD_{540}H_2O$)×100%.

2.5. Plasma Stability

405 µl of plasma/albumin solution were placed in a polypropylene (PP) tube and spiked with 45 µl of compound from a 100 mM solution B, derived from 135 µl of PBS and 15 µl of 1 mM peptide in PBS, pH 7.4. 150 µl aliquots were transferred into individual wells of the 10 kDa filter plate (Millipore MAPPB 1010 Biomax membrane). For "0 minutes controls": 270 µl of PBS were placed in a PP tube and 30 µl of stock solution B was added and mixed. 150 µl of control solution were placed into one well of the filter plate and served as "filtered control".

Further 150 µl of control solution were placed directly into a receiver well (reserved for filtrate) and served as "not-filtered control". The entire plate including evaporation lid was incubated for 60 min at 37° C. Plasma samples (rat plasma: Harlan Sera lab UK, human plasma: Blutspendezentrum ZÜrich) were centrifuged at least for 2 h at 4300 rpm (3500 g) and 15° C. in order to yield 100 µl filtrate. For "serum albumin"-samples (freshly prepared human albumin: Sigma A-4327, rat albumin: Sigma A-6272, all at 40 mg/ml concentration in PBS) approximately 1 hour of centrifugation was sufficient. The filtrates in the receiver PP plate were analysed by LC/MS as follows: Column: Jupiter C18 (Phenomenex), mobile phases: (A) 0.1% formic acid in water and (B) acetonitrile, gradient: 5%-100% (B) in 2 minutes, electrospray ionization, MRM detection (triple quadrupole). The peak areas were determined and triplicate values were averaged. The binding was expressed in percent of the (filtered and not-filtered time point 0 min) control 1 and 2 by: 100-(100×$T_{60}$/To). The average from these values was then calculated.

2.6. Pharmacokinetic Study (PK)

Pharmacokinetic Study after Single Intravenous, Subcutaneous and Intraperitoneal Administration in Mice Pharmacokinetic study after single intravenous (i.v.) and subcutaneous (s.c.) administration was performed for the compound of Example 1 ("Ex. 1"). CD-1 mice (20-25 g) were used in the study. Physiological saline was used a vehicle. The volume was 2 ml/kg i.v., and 5 ml/kg s.c. and the peptide Ex. 1 was injected to give a final intravenous dose of 1 mg/kg, and a subcutaneous dose of 5 mg/kg. Approximately 200-250 µl of blood was removed under light isoflurane anesthesia by cardiac puncture at predetermined time intervals (0, 5, 15, 30 min and 1, 2, 3, 4 and 5 hours for the i.v. study and 0, 15, 30 min and 1, 2, 4, 6, 8 and 10 hours for the s.c. study) and added to heparinized tubes. Plasma was removed from pelleted cells upon centrifugation and frozen at −80° C. prior to HPLC-MS analysis.

Preparation of the Plasma Calibration Samples

"Blank" mouse plasma from untreated animals was used. Aliquots of plasma of 0.2 ml each were spiked with 50 ng of propranolol (Internal Standard, IS), (sample preparation by solid phase extraction on OASIS® HLB cartridges (Waters)) and with known amounts of Ex. 1 in order to obtain 9 plasma calibration samples in the range 10-5000 nM. The OASIS® HLB cartridges were conditioned with 1 ml of methanol and then with 1 ml of 1% $NH_3$ in water. Samples were then diluted with 700 µl of 1% $NH_3$ in water and loaded. The plate was washed with 1 ml of methanol/1% $NH_3$ in water 5/95. Elution was performed using 1 ml of 0.1% TFA in methanol.

The plate containing eluates was introduced into the concentrator system and taken to dryness. The residues were dissolved in 100 µL of formic acid 0.1%/acetonitrile, 95/5 (v/v) and analysed in the HPLC/MS on a reverse phase analytical column (Jupiter C18, 50×2.0 mm, 5 µm, Phenomenex), using gradient elution (mobile phases A: 0.1% formic acid in water, B: Acetonitrile; from 5% B to 100% B in 2 min.).

Preparation of Plasma Samples

Samples coming from animal treatments were pooled in order to obtain an appropriate volume for the extraction. If the total volume obtained was less than 0.2 ml the appropriate amount of "blank" mouse plasma was added in order to keep the matrix identical to the calibration curve. Samples were than spiked with IS and processed as described for the calibration curve.

Pharmacokinetic Evaluation

PK analysis was performed on pooled data (generally n=2 or 3) using the software Win Nonlin (Pharsight). The area under the curve AUC was calculated by the linear trapezoidal rule. Elimination half-life was calculated by the linear regression on at least three data points during the elimination phase. The time intervals selected for the half-life determinations were evaluated by the correlation coefficient ($r^2$), which should be at least above 0.85 and most optimally above 0.96. In case of i.v. administration the initial concentration at $t_{zero}$ was determined by extrapolation of the curve through the first two time points. Finally bioavailability after i.p. administration was calculated from the normalised AUCinf_D_obs ration after s.c. versus i.v. administration.

2.7. In Vivo Septicemia Assay

Groups of 6 CD-1 (Crl.) derived male mice weighing 24±2 g were used. The mice were each inoculated intravenously (IV) with an LD90-100 of Pseudomonas aeruginosa (ATCC 27853) (9×106 CFU/0.5 ml/mouse) in brain heart infusion broth without 5% mucin. Compound at doses of 5, 2.5, 1, 0.5, 0.25 and 0.1 mg/kg, vehicle (0.9% NaCl, 10 ml/kg) was administered subcutaneously (SC) to test animals at 1 hour after bacterial inoculation. Also, an additional group was treated twice with compound at a dose of 5 mg/kg at 1 and 6 hours after bacterial inoculation. Mortality was recorded once daily for 7 days following the bacterial inoculation and an increase of survival of the animals by 50 percent or more ($^3$ 50%) after the bacterial inoculation, relative to vehicle control, indicates significant antimicrobial effect. The MED (ED50) was determined by nonlinear regression using Graph-Pad Prism (Graph Pad Software, USA).

2.8. Results

The results of the experiments described in 2.2, 2.3 and 2.4, above, are indicated in Table 2, herein below

TABLE 2

Minimal inhibitory concentrations (MIC in µg/ml) in Mueller-Hinton broth, cytotoxicity and percentage hemolyses at a concentration of 100 µg/ml of peptide

| Ex. | P. aeruginosa ATCC 27853 | P. aeruginosa P8191900 | P. aeruginosa P1021903 | P. aeruginosa P1021913 | P. aeruginosa IMP1 Livermore 3140 | Average MIC | Cytotoxicity $GI_{50}$ Hela cells | Hemolysis at 100 µg/ml |
|---|---|---|---|---|---|---|---|---|
| 1 | 0.03 | 0.07 | 0.07 | 0.13 | 0.18 | 0.10 | 30 | 0.5 |
| 2 | 0.04 | 0.10 | 0.16 | 0.18 | 0.24 | 0.15 | 50 | 0.3 |
| 3 | 0.09 | 0.30 | 0.30 | 0.31 | 2.0 | 0.6 | 34 | 0.6 |
| 4 | 0.75 | 1.50 | 1.50 | 2.50 | >2.0 | >1 | 40 | 0.6 |
| 5 | 0.08 | 0.30 | 0.21 | 0.21 | 0.75 | 0.31 | 50 | 0.6 |
| 6 | 0.05 | 0.10 | 0.09 | 0.16 | 0.24 | 0.13 | 50 | 0.2 |
| 7 | 0.13 | 0.50 | 1.50 | 0.65 | >2 | >1 | 13 | 0.8 |
| 8 | 0.05 | 0.18 | 0.18 | 0.31 | 0.43 | 0.23 | 50 | 0 |
| 9 | 0.21 | 0.75 | 1.50 | 0.75 | >2 | >1 | 50 | 0.7 |
| 10 | 0.05 | 0.18 | 0.13 | 0.37 | 0.43 | 0.23 | 50 | 0 |
| 11 | 0.30 | 1.00 | 2.00 | 0.75 | >2 | >1 | 50 | 0.5 |
| 12 | 0.40 | 1.00 | 2.00 | 0.75 | >2 | >1 | 50 | 0.7 |
| 13 | 0.21 | 0.30 | 0.40 | 0.31 | 0.75 | 0.40 | 50 | 0.4 |
| 14 | 0.21 | 0.40 | 0.31 | 0.65 | >2 | >1 | 12 | 0.3 |
| 15 | 0.50 | 2.50 | 1.25 | 2.25 | >2 | >1 | 50 | 0.3 |
| 16 | 0.05 | 0.09 | 0.05 | 0.10 | 0.24 | 0.11 | 50 | 0.1 |
| 17 | 0.75 | 1.50 | 2.00 | 1.25 | >2 | >1 | 29 | 0.5 |
| 18 | 0.06 | 0.10 | 0.10 | 0.81 | 0.30 | 0.28 | 50 | 0.4 |
| 19 | 0.03 | 0.05 | 0.03 | 0.10 | 0.10 | 0.06 | 50 | 0.2 |
| 20 | 0.21 | 0.40 | 0.21 | 0.31 | 1.25 | 0.48 | 50 | 0.2 |
| 21 | 0.09 | 0.40 | 0.21 | 0.31 | 1.00 | 0.40 | 50 | 0.4 |
| 22 | 0.02 | 0.09 | 0.09 | 0.16 | 0.24 | 0.12 | 50 | 0.2 |
| 23 | 1.00 | 1.00 | 1.50 | 1.25 | >2 | >1 | 13 | 0.5 |
| 24 | 0.05 | 0.16 | 0.08 | 0.16 | 0.24 | 0.14 | 50 | 0.1 |

TABLE 2-continued

Minimal inhibitory concentrations (MIC in µg/ml) in Mueller-Hinton broth, cytotoxicity and percentage hemolyses at a concentration of 100 µg/ml of peptide

| Ex. | P. aeruginosa ATCC 27853 | P. aeruginosa P8191900 | P. aeruginosa P1021903 | P. aeruginosa P1021913 | P. aeruginosa IMP1 Livermore 3140 | Average MIC | Cytotoxicity $GI_{50}$ Hela cells | Hemolysis at 100 µg/ml |
|---|---|---|---|---|---|---|---|---|
| 25 | 0.05 | 0.10 | 0.05 | 0.13 | 0.24 | 0.11 | 50 | 0.1 |
| 26 | 0.08 | 0.30 | 0.13 | 0.18 | 0.40 | 0.22 | 50 | 0.8 |
| 27 | 0.09 | 0.30 | 0.30 | 0.21 | 0.50 | 0.28 | 50 | 0.6 |
| 28 | 0.04 | 0.10 | 0.07 | 0.16 | 0.24 | 0.12 | 50 | 0.1 |
| 29 | 0.09 | 0.13 | 0.13 | 0.21 | 0.40 | 0.19 | 50 | 0.5 |
| 30 | 0.09 | 0.13 | 0.30 | 0.50 | 2.00 | 0.60 | 46 | 0.5 |
| 31 | 0.03 | 0.16 | 0.40 | 0.16 | 0.24 | 0.20 | 50 | 0.5 |
| 32 | 0.02 | 0.05 | 0.05 | 0.10 | 0.22 | 0.09 | 50 | 0 |
| 33 | 0.05 | 0.18 | 0.29 | 0.31 | 0.43 | 0.25 | 50 | 0.1 |
| 34 | 0.05 | 0.24 | 0.29 | 0.48 | 0.60 | 0.33 | 50 | 0 |
| 35 | 0.05 | 0.22 | 0.10 | 0.24 | 0.31 | 0.18 | 48 | 0.2 |
| 36 | 0.06 | 0.18 | 0.18 | 0.24 | 0.43 | 0.22 | 50 | 0.1 |
| 37 | 0.06 | 0.18 | 0.31 | 0.37 | 1.17 | 0.42 | 50 | 0.5 |
| 38 | 0.09 | 0.17 | 0.17 | 0.27 | 1.06 | 0.35 | 50 | 0.5 |
| 39 | 0.13 | 0.21 | 0.31 | 0.31 | 0.75 | 0.34 | 50 | 0.4 |
| 40 | 0.25 | 0.50 | 0.50 | 0.50 | 1.00 | 0.55 | 50 | 0.7 |
| 41 | 0.02 | 0.05 | 0.03 | 0.25 | 0.25 | 0.12 | 50 | 0.2 |
| 42 | 0.25 | 0.06 | 0.125 | 0.50 | 0.50 | 0.29 | 50 | 0.2 |
| 43 | 0.13 | 0.50 | 0.125 | 2.00 | 2.00 | 0.95 | 50 | 0.5 |
| 45 | 0.25 | 0.50 | 0.50 | 1.00 | 1.00 | 0.65 | 50 | 0.2 |
| 46 | 0.06 | 0.25 | 0.25 | 0.50 | 0.50 | 0.31 | 50 | 0.3 |
| 47 | 0.09 | 0.13 | 0.13 | 0.50 | 0.75 | 0.32 | 50 | 0.2 |
| 48 | 0.02 | 0.03 | 0.02 | 0.13 | 0.19 | 0.08 | 50 | 0.2 |
| 49 | 0.03 | 0.06 | 0.03 | 0.25 | 0.50 | 0.17 | 50 | 0.1 |
| 50 | 0.09 | 0.13 | 0.06 | 0.50 | 2.00 | 0.56 | 50 | n.d. | n.d. = not determined

The results of the experiment described in 2.5, above, are indicated in Table 3 herein below.

TABLE 3

| Ex. | Stability human Plasma $t_{1/2}$ (min) | Stability rat Plasma $t_{1/2}$ (min) |
|---|---|---|
| 1 | 300 | 300 |
| 2 | 300 | 300 |
| 6 | 300 | 300 |
| 16 | 300 | 300 |
| 22 | 300 | 300 |
| 24 | 300 | 300 |
| 25 | 300 | 300 |
| 28 | 300 | 300 |
| 29 | 300 | 300 |
| 32 | 300 | 300 |
| 35 | 300 | 300 |

The results of the experiment described in 2.6 (PK), above, are indicated in Table 4 herein below.

TABLE 4

| | | Administration route | |
|---|---|---|---|
| Parameters | Dimensions | I.V. | S.C. |
| HL_Lambda_z | hr | 0.53 | 0.95 |
| Tmax | hr | 0.08 | 0.58 |
| Cmax | ng/mL | 1268.0 | 2333.3 |
| Cmax_D | kg * ng/mL/mg | 1268.0 | 466.7 |
| C0 | ng/mL | 2174.0 | — |
| AUCINF_obs | hr * ng/mL | 679.5 | 4016.5 |
| AUCINF_D_obs | hr * kg * ng/mL/mg | 679.5 | 803.3 |
| Vz_obs | mL/kg | 1136.1 | 1705.6 |
| Cl_obs | mL/hr/kg | 1539.1 | 1249.8 |
| Bioavailability | % | 100 | 118.2 |

After intravenous administration of Ex. 1 at a dose level of 1 mg/kg body weight, Ex. 1 followed intravenous kinetic characteristics. After PK analysis, Ex. 1 showed an extrapolated $C_{initial}$ of 2174 ng/ml and a $C_{max}$ observed of 1268 ng/ml at 5 min. Plasma levels rapidly decreased to 575 and 177 ng/ml at 15 min and 1 hour respectively. From 0.5 to 2 h plasma levels decreased with an elimination half-life of 0.53 h to 10.6 ng/ml at 3 h. The AUCINF_obs amounted to 679.5 ng·h/ml.

After subcutaneous administration of Ex. 1 at a dose level of 5 mg/kg body weight, plasma levels of Ex. 1 increased the first 0.5-1 h and showed a $C_{max}$ of 2333 ng/ml. From 0.5 to 8 h plasma levels decreased with an elimination half-life of 0.95 h to 7.3 ng/ml at 8 h. The AUCINF_obs amounted to 4016.5 ng·h/ml.

As compared to the normalized AUC value after i.v. administration (100% absorbed, 679 ng·h/ml) of Ex. 1 absorbed after s.c. administration amounted to 118% (803 ng·h/ml). The value above 100% may partially reflect an impaired reliability caused by the limited number of points or is caused by a non-linearity in dose.

The results of the experiment described in 2.7 (Septicaemia Assay), above, are indicated in Table 5-7 herein below.

Septicaemia experiment in mice: LD90-100 of *Pseudomonas aeruginosa*

(ATCC 27853) (9×10$^6$ CFU/0.5 ml/mouse IV and after 1 h Ex. 1 s.c.

TABLE 5

| Compound/dose | Dead | Survivors |
|---|---|---|
| Negative control | 5 | 1 |
| Gentamycin, 1 mg/kg | 0 | 6 |

TABLE 5-continued

| Compound/dose | Dead | Survivors |
|---|---|---|
| Compound of Example 1 in following doses (mg/kg) | | |
| 10 (2 × 5) | 0 | 6 |
| 5 | 0 | 6 |
| 2.5 | 0 | 6 |
| 1 | 1 | 5 |
| 0.5 | 2 | 4 |
| 0.25 | 5 | 1 |
| 0.1 | 5 | 1 |

Septicaemia experiment in mice: LD90-100 of *Pseudomonas aeruginosa*
(ATCC 27853) (9×106 CFU/0.5 ml/mouse IV), and after 1 and 5 h Ex. 40 s.c.

TABLE 6

| Compound/dose | Dead | Survivors |
|---|---|---|
| Negative control | 6 | 0 |
| Gentamycin, 2 × 1 mg/kg | 1 | 5 |
| Compound of Example 40 in following doses (mg/kg) | | |
| 2 × 10 | 0 | 6 |
| 2 × 3 | 0 | 6 |
| 2 × 1 | 2 | 4 |
| 2 × 0.3 | 6 | 0 |
| 2 × 0.1 | 6 | 0 |

Septicaemia experiment in mice: LD90-100 of *Pseudomonas aeruginosa*
(ATCC 27853) (9×106 CFU/0.5 ml/mouse IV), and after 1 and 5 h Ex. 50 s.c.

TABLE 7

| Compound/dose | Dead | Survivors |
|---|---|---|
| Negative control | 5 | 1 |
| Gentamycin, 2 × 1 mg/kg | 1 | 5 |
| Compound of Example 50 in following doses (mg/kg) | | |
| 2 × 10 | 0 | 6 |
| 2 × 3 | 3 | 3 |
| 2 × 1 | 5 | 1 |
| 2 × 0.3 | 6 | 0 |
| 2 × 0.1 | 6 | 0 |

REFERENCES

1. National Committee for Clinical Laboratory Standards. 1993. Methods for dilution antimicrobial susceptibility tests for bacteria that grow aerobically, 3rd ed. Approved standard M7-A3. National Committee for Clinical laboratory standards, Villanova, Pa.
2. Mossman T. J Immunol Meth 1983, 65, 55-63
3. Berridge M V, Tan A S. *Archives of Biochemistry &Biophysics* 1993, 303, 474-482

The invention claimed is:
1. A method of treating a disease or infection caused by a *Pseudomonas aeruginosa* comprising administering to a subject in need thereof an effective amount of a compound represented by formula (I):

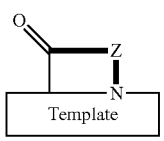

wherein

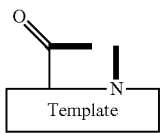

is $^D$Pro-$^L$Pro or $^L$Pro-$^D$Pro and Z is a chain of 12 α-amino acid residues, wherein the positions of the amino acid residues in the chain are counted starting from the N-terminal amino acid, wherein the amino acid residues in positions P1 to P12 of the chain are:

Thr, Trp, Ile, Dab, Lys, Dab, Dab, Trp, Dab, Dab, Ala, Dab;
Thr, Trp, Ile, Dab, Lys, Dab, Dab, Trp, Dab, Dab, Gly, Dab;
Thr, Trp, Ile, Dab, Lys, Dab, Dab, Trp, Dab, Dab, $^D$Ala, Dab;
Thr, Trp, Ile, Dab, Lys, Dab, Dab, Trp, Dab, Dab, $^D$Val, Dab;
Thr, Trp, Ile, Dab, Lys, Dab, Dab, Trp, Dab, Dab, Aib, Dab;
Thr, Trp, Ile, Dab, Lys, Dab, Dab, Trp, Dab, Dab, Abu, Dab;
Thr, Trp, Ile, Dab, Lys, Dab, Dab, Trp, Dab, Dab, Leu, Dab;
Thr, Trp, Ile, Dab, Lys, Dab, Dab, Trp, Dab, Dab, Ile, Dab;
Thr, Trp, Ile, Dab, Lys, Dab, Dab, Trp, Dab, Dab, Nle, Dab;
Thr, Trp, Ile, Dab, Lys, Dab, Dab, Trp, Dab, Dab, Nva, Dab;
Thr, Trp, Ile, Dab, Lys, Dab, Dab, Trp, Dab, Dab, Chg, Dab;
Thr, Trp, Ile, Dab, Lys, Dab, Dab, Trp, Dab, Dab, Cha, Dab;
Thr, Trp, Ile, Dab, Lys, Dab, Dab, Trp, Dab, Dab, Gln, Dab;
Thr, Trp, Ile, Dab, Lys, Dab, Dab, Trp, Dab, Dab, Asp, Dab;
Thr, Trp, Ile, Dab, Lys, Dab, Dab, Trp, Dab, Dab, Glu, Dab;
Thr, Trp, Ile, Dab, Lys, Dab, Dab, Trp, Dab, Dab, Thr, Dab;
Thr, Trp, Ile, Dab, Lys, Dab, Dab, Trp, Dab, Dab, Pro, Dab;
Cit, Trp, Ile, Dab, Lys, Dab, Dab, Trp, Dab, Dab, Ala, Dab;
Thr, Tyr, Ile, Dab, Lys, Dab, Dab, Trp, Dab, Dab, Ala, Dab;
Thr, Trp, Ile, Dab, Lys, Dab, Dab, Tyr, Dab, Dab, Ala, Dab;
Thr, Trp, Ile, Dab, Lys, Dab, His, Trp, Dab, Dab, Ala, Dab;
Ala, Trp, Ile, Dab, Lys, Dab, Dab, Trp, Dab, Dab, Ala, Dab;
Ala, Trp, Ile, Dab, Dab, Dab, Dab, Trp, Dab, Dab, Val, Dab;
Thr, Trp, Ile, Lys, Lys, Dab, Dab, Trp, Dab, Dab, Ala, Dab;
Thr, Trp, Ile, Dab, Lys, Lys, Dab, Trp, Dab, Dab, Ala, Dab;
Thr, Trp, Ile, Dab, Lys, Dab, Lys, Trp, Dab, Dab, Ala, Dab;
Thr, Trp, Ile, Dab, Lys, Dab, Dab, Trp, Lys, Dab, Ala, Dab;
Thr, Trp, Ile, Dab, Lys, Dab, Dab, Trp, Dab, Dab, Ala, Lys;
Thr, Trp, Ile, Gln, Lys, Dab, Dab, Trp, Dab, Dab, Ala, Dab;
Thr, Trp, Ile, Gln, Lys, Dab, Dab, Trp, Dab, Dab, Val, Dab;
Thr, Trp, Nle, Dab, Lys, Dab, Dab, Trp, Dab, Dab, Ala, Dab;
Thr, Trp, Val, Dab, Lys, Dab, Dab, Trp, Dab, Dab, Ala, Dab;
Thr, Trp, Chg, Dab, Lys, Dab, Dab, Trp, Dab, Dab, Ala, Dab;
Thr, Trp, Cha, Dab, Lys, Dab, Dab, Trp, Dab, Dab, Ala, Dab;
Thr, Trp, Ile, Dab, Lys, Dab, Dab, Trp, Dab, Dab, Hse, Dab;
Thr, Trp, Ile, Dab, Lys, Dab, Dab, Trp, Dab, Dab, t-BuG, Dab;
Thr, Trp, Ile, Dab, Lys, Dab, Dab, Trp, Dab, Dab, Cpa, Dab;
Thr, Trp, Ile, Dab, Lys, Dab, Dab, Trp, Dab, Dab, Asn, Dab;
Thr, Trp, Ile, Dab, Lys, Dab, Gln, Trp, Dab, Dab, Ala, Dab;
Thr, Trp, Ile, Gln, Lys, Dab, Dab, Trp, Dab, Dab, Ala, Gln;
Thr, Trp, Ile, Dab, Lys, $^D$Dab, Dab, Trp, Dab, Dab, Ala, Dab;
Asp, Tyr, Ile, Dab, Lys, $^D$Da, Dab, Trp, Dab, Dab, Ala, Dab;
Asp, Tyr, Ile, Dab, Orn, $^D$Dab, Dab, Trp, Dab, Dab, Ala, Dab;
Glu, Trp, Ile, Dab, Lys, $^D$Dab, Dab, Trp, Dab, Dab, Ala, Dab;
Glu, Trp, Ile, Dab, Lys, $^D$Dab, Dab, Trp, Dab, Dab, Ala, Gln;
Glu, Trp, Ile, Dab, Lys, $^D$Dab, Dab, Trp, Dab, Dab, Ala, Dap;
Glu, Trp, Ile, Dab, Orn, $^D$Dab, Dab, Trp, Dab, Dab, Ala, Dab;
Thr, Trp, Ile, Dab, Orn, $^D$Dab, Dab, Trp, Dab, Dab, Ala, Dab; or
Glu, Trp, Ile, Gln, Lys, Dab, Dab, Ser, Dab, Dab, Ala, Ser, or a pharmaceutically acceptable salt or enantiomer thereof.

2. The method of claim 1, wherein the subject is suffering from at least one disease selected from the group consisting of respiratory diseases, skin or soft tissue diseases, gastrointestinal diseases, eye diseases, ear diseases, CNS diseases, bone diseases, cardiovascular diseases, gastrourinal diseases, cancer and HIV.

3. The method of claim 1, wherein the subject is suffering from at least one disease selected from the group consisting of cystic fibrosis, emphysema, asthma, surgical wounds, traumatic wounds, burn wounds, epidemic diarrhea, necrotizing enterocolitis, typhlitis, keratitis, endophthalmitis, otitis, brain abscess, meningitis, osteochondritis, osteomyelitis, endocartitis, pericarditis, epididymitis, prostatitis, urethritis, cancer and HIV.

4. The method of claim 1, wherein the *Pseudomonas aeruginosa* bacteria is multi-drug resistant.

5. The method of claim 1, wherein the compound represented by formula (I) is administered in the form of a pharmaceutical composition and wherein the pharmaceutical composition further comprises at least one member selected from the group consisting of carriers, diluents, excipients and auxiliaries.

6. The method of claim 1, wherein at least one additional pharmaceutical agent is administered to the subject.

7. The method of claim 6, wherein the additional pharmaceutical agent is selected from the group consisting of antimicrobial agents, antibiotic agents, anti cancer agents and antiviral agents.

8. The method of claim 1, wherein the compound of formula (I) is administered topically.

9. The method of claim 1, wherein the compound of formula (I) is administered by injection.

10. The method of claim 1, wherein the compound of formula (I) is administered transdermally, transmucosally, orally or by pulmonary administration.

* * * * *

SEQUENCE LISTING

```
<160> NUMBER OF SEQ ID NOS: 50

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 1

Thr Trp Ile Xaa Lys Xaa Xaa Trp Xaa Xaa Ala Xaa Pro Pro
1               5                   10

<210> SEQ ID NO 2
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 2

Thr Trp Ile Xaa Lys Xaa Xaa Trp Xaa Xaa Gly Xaa Pro Pro
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: D-Ala
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 3

Thr Trp Ile Xaa Lys Xaa Xaa Trp Xaa Xaa Ala Xaa Pro Pro
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: D-Val
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 4

Thr Trp Ile Xaa Lys Xaa Xaa Trp Xaa Xaa Val Xaa Pro Pro
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 5

Thr Trp Ile Xaa Lys Xaa Xaa Trp Xaa Xaa Xaa Xaa Pro Pro
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
```

```
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Abu
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 6

Thr Trp Ile Xaa Lys Xaa Xaa Trp Xaa Xaa Xaa Xaa Pro Pro
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 7

Thr Trp Ile Xaa Lys Xaa Xaa Trp Xaa Xaa Leu Xaa Pro Pro
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
```

```
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 8

Thr Trp Ile Xaa Lys Xaa Xaa Trp Xaa Xaa Ile Xaa Pro Pro
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Nle
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 9

Thr Trp Ile Xaa Lys Xaa Xaa Trp Xaa Xaa Xaa Xaa Pro Pro
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Nva
<220> FEATURE:
<221> NAME/KEY: MOD_RES
<222> LOCATION: (12)..(12)
```

```
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 10

Thr Trp Ile Xaa Lys Xaa Xaa Trp Xaa Xaa Xaa Xaa Pro Pro
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Chg
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 11

Thr Trp Ile Xaa Lys Xaa Xaa Trp Xaa Xaa Xaa Xaa Pro Pro
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
```

```
<222> LOCATION: (13)..(13)
<223> OTHER INFORMATION: D-Pro

<400> SEQUENCE: 12

Thr Trp Ile Xaa Lys Xaa Xaa Trp Xaa Xaa Xaa Xaa Pro Pro
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 13

Thr Trp Ile Xaa Lys Xaa Xaa Trp Xaa Xaa Gln Xaa Pro Pro
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 14

Thr Trp Ile Xaa Lys Xaa Xaa Trp Xaa Xaa Asp Xaa Pro Pro
1               5                   10

<210> SEQ ID NO 15
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 15

Thr Trp Ile Xaa Lys Xaa Xaa Trp Xaa Xaa Glu Xaa Pro Pro
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 16

Thr Trp Ile Xaa Lys Xaa Xaa Trp Xaa Xaa Thr Xaa Pro Pro
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
```

```
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 17

Thr Trp Ile Xaa Lys Xaa Xaa Trp Xaa Xaa Pro Xaa Pro Pro
 1               5                  10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cit
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 18

Xaa Trp Ile Xaa Lys Xaa Xaa Trp Xaa Xaa Ala Xaa Pro Pro
 1               5                  10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
```

```
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 19

Thr Tyr Ile Xaa Lys Xaa Xaa Trp Xaa Xaa Ala Xaa Pro Pro
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 20

Thr Trp Ile Xaa Lys Xaa Xaa Tyr Xaa Xaa Ala Xaa Pro Pro
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 21

Thr Trp Ile Xaa Lys Xaa His Trp Xaa Xaa Ala Xaa Pro Pro
```

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 22

Ala Trp Ile Xaa Lys Xaa Xaa Trp Xaa Xaa Ala Xaa Pro Pro
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 23

Ala Trp Ile Xaa Xaa Xaa Xaa Trp Xaa Xaa Val Xaa Pro Pro
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Dab
<220> FEATURE:

```
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 24

Thr Trp Ile Lys Lys Xaa Xaa Trp Xaa Xaa Ala Xaa Pro Pro
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 25

Thr Trp Ile Xaa Lys Lys Xaa Trp Xaa Xaa Ala Xaa Pro Pro
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro
```

```
<400> SEQUENCE: 26

Thr Trp Ile Xaa Lys Xaa Lys Trp Xaa Xaa Ala Xaa Pro Pro
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (10)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 27

Thr Trp Ile Xaa Lys Xaa Xaa Trp Lys Xaa Ala Xaa Pro Pro
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 28

Thr Trp Ile Xaa Lys Xaa Xaa Trp Xaa Xaa Ala Lys Pro Pro
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 29

Thr Trp Ile Gln Lys Xaa Xaa Trp Xaa Xaa Ala Xaa Pro Pro
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 30

Thr Trp Ile Gln Lys Xaa Xaa Trp Xaa Xaa Val Xaa Pro Pro
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
```

```
<220> FEATURE:
<221> NAME/KEY: MOD_RES
<222> LOCATION: (13)..(13)
<223> OTHER INFORMATION: D-Pro

<400> SEQUENCE: 31

Thr Trp Xaa Xaa Lys Xaa Xaa Trp Xaa Xaa Ala Xaa Pro Pro
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 32

Thr Trp Val Xaa Lys Xaa Xaa Trp Xaa Xaa Ala Xaa Pro Pro
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 33
```

-continued

```
Thr Trp Xaa Xaa Lys Xaa Xaa Trp Xaa Xaa Ala Xaa Pro Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cha
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 34

Thr Trp Xaa Xaa Lys Xaa Xaa Trp Xaa Xaa Ala Xaa Pro Pro
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Hse
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 35

Thr Trp Ile Xaa Lys Xaa Xaa Trp Xaa Xaa Xaa Xaa Pro Pro
1               5                   10
```

```
<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: t-BuGly
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 36

Thr Trp Ile Xaa Lys Xaa Xaa Trp Xaa Xaa Gly Xaa Pro Pro
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (11)..(11)
<223> OTHER INFORMATION: Cpa
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 37

Thr Trp Ile Xaa Lys Xaa Xaa Trp Xaa Xaa Xaa Xaa Pro Pro
1               5                   10

<210> SEQ ID NO 38
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 38

Thr Trp Ile Xaa Lys Xaa Xaa Trp Xaa Xaa Asn Xaa Pro Pro
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 39

Thr Trp Ile Xaa Lys Xaa Gln Trp Xaa Xaa Ala Xaa Pro Pro
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
```

```
<222> LOCATION: (9)..(10)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 40

Thr Trp Ile Gln Lys Xaa Xaa Trp Xaa Xaa Ala Gln Pro Pro
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 41

Thr Trp Ile Xaa Lys Xaa Xaa Trp Xaa Xaa Ala Xaa Pro Pro
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
```

```
<221> NAME/KEY: MOD_RES
<222> LOCATION: (13)..(13)
<223> OTHER INFORMATION: D-Pro

<400> SEQUENCE: 42

Asp Tyr Ile Xaa Lys Xaa Xaa Trp Xaa Xaa Ala Xaa Pro Pro
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 43

Asp Tyr Ile Xaa Xaa Xaa Xaa Trp Xaa Xaa Ala Xaa Pro Pro
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
```

```
<220> FEATURE:
<221> NAME/KEY: MOD_RES
<222> LOCATION: (13)..(13)
<223> OTHER INFORMATION: D-Pro

<400> SEQUENCE: 44

Glu Trp Ile Xaa Lys Xaa Xaa Trp Xaa Xaa Ala Xaa Pro Pro
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 45

Glu Trp Ile Xaa Lys Xaa Xaa Trp Xaa Xaa Ala Gln Pro Pro
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dap
<220> FEATURE:
<221> NAME/KEY: MOD_RES
<222> LOCATION: (13)..(13)
<223> OTHER INFORMATION: D-Pro

<400> SEQUENCE: 46
```

```
Glu Trp Ile Xaa Lys Xaa Xaa Trp Xaa Xaa Ala Xaa Pro Pro
1               5                   10
```

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 47

```
Glu Trp Ile Xaa Xaa Xaa Xaa Trp Xaa Xaa Ala Xaa Pro Pro
1               5                   10
```

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (12)..(12)
<223> OTHER INFORMATION: Dab
<220> FEATURE:
<221> NAME/KEY: MOD_RES

```
<222> LOCATION: (13)..(13)
<223> OTHER INFORMATION: D-Pro

<400> SEQUENCE: 48

Thr Trp Ile Xaa Xaa Xaa Xaa Trp Xaa Xaa Ala Xaa Pro Pro
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: D-Dab
<220> FEATURE:
<221> NAME/KEY: MOD_RES
<222> LOCATION: (7)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 49

Thr Trp Ile Xaa Xaa Xaa Xaa Trp Xaa Xaa Ala Ser Pro Pro
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Dab
<220> FEATURE:
<221> NAME/KEY: MOD_RES
<222> LOCATION: (9)..(10)
<223> OTHER INFORMATION: Dab
<220> FEATURE:
<221> NAME/KEY: MOD_RES
<222> LOCATION: (13)..(13)
<223> OTHER INFORMATION: D-Pro

<400> SEQUENCE: 50

Glu Trp Ile Gln Lys Xaa Xaa Ser Xaa Xaa Ala Ser Pro Pro
1               5                   10
```

UNITED STATES PATENT AND TRADEMARK OFFICE
CERTIFICATE OF CORRECTION

PATENT NO. : 9,596,852 B2
APPLICATION NO. : 14/175193
DATED : March 21, 2017
INVENTOR(S) : Steven J. Demarco et al.

It is certified that error appears in the above-identified patent and that said Letters Patent is hereby corrected as shown below:

Column 71, Line 60:
"$CH_2CH_2$" should read --$CH_2Cl_2$--.

Column 72, Line 30:
"$CH_2CH_2/MeOH$" should read --$CH_2Cl_2/MeOH$--.

Column 75, Line 59:
"fβ-hairpin" should read --β-hairpin--.

Column 77, Lines 57, 61, 63, 64, 65, and 66:
"$CH_2CH_2$" should read --$CH_2Cl_2$--.

Column 78, Lines 50, 52, 54, 55, 61, and 62:
"$CH_2CH_2$" should read --$CH_2Cl_2$--.

Signed and Sealed this
Tenth Day of April, 2018

Andrei Iancu
*Director of the United States Patent and Trademark Office*